(12) United States Patent
Sullivan

(10) Patent No.: US 10,711,278 B2
(45) Date of Patent: Jul. 14, 2020

(54) GENETICALLY ALTERED ALFALFA PRODUCING CLOVAMIDE AND/OR RELATED HYDROXYCINNAMOYL AMIDES

(71) Applicant: The United States of America, as represented by the Secretary of Agriculture, Washington, DC (US)

(72) Inventor: Michael L Sullivan, Madison, WI (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 16/275,450

(22) Filed: Feb. 14, 2019

(65) Prior Publication Data

US 2020/0010843 A1 Jan. 9, 2020

Related U.S. Application Data

(62) Division of application No. 15/274,050, filed on Sep. 23, 2016, now Pat. No. 10,253,324.

(60) Provisional application No. 62/234,720, filed on Sep. 30, 2015.

(51) Int. Cl.
| | | |
|---|---|---|
| *C12N 15/82* | (2006.01) | |
| *C12Q 1/6895* | (2018.01) | |
| *C12N 9/10* | (2006.01) | |

(52) U.S. Cl.
CPC ....... *C12N 15/8243* (2013.01); *C12N 9/1029* (2013.01); *C12N 15/8251* (2013.01); *C12Q 1/6895* (2013.01); *C12Y 203/01* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 8,338,339 B2 | 12/2012 | Hatfield et al. |
| 2013/0078683 A1 | 3/2013 | Loque et al. |
| 2014/0298539 A1 | 10/2014 | Loque et al. |
| 2015/0013033 A1 | 1/2015 | Loque et al. |
| 2016/0017355 A1 | 1/2016 | Loque et al. |

OTHER PUBLICATIONS

Trifolium pratense L-DOPA N-hydroxycinnamoyl transferase (HDT1) mRNA, GenBank accession No. MF115997, published Oct. 1, 2018.*
Trifolium pratense L-DOPA N-hydroxycinnamoyl transferase (HDT2) mRNA, with a GenBank accession No. MF115998, published Oct. 1, 2018.*
Katepa-Mupondwa, Felicitas M. et al., An improved breeding strategy for autotetraploid alfalfa (*Medicago sativa* L.), Euphytica, (2002), 123:139-146.
Li, Xuehui et al., Applied Genetics and Genomics in Alfalfa Breeding, Agronomy, (2012), 2:40-61.
The Phytochemical Society of North America, University of Illinois at Urbana-Champaign, PSNA-online.org, PSNA (2015), pp. 1-92.
Sullivan, Michael L et al., Efficacy of various naturally occurring caffeic acid derivatives in preventing post-harvest protein losses in forages†, J Sci Food Agric, (2013); 93:219-226.
Sullivan, Michael L et al., A Novel Red Clover Hydroxycinnamoyl Transferase Has Enzymatic Activities Consistent with a Role in Phaselic Acid Biosynthesis1[OA], Plant Physiology, (2009), 150:1866-1879.
Sullivan, Michael L et al., Perennial peanut (*Arachis glabrata* Benth.) leaves contain hydroxycinnamoyl-CoA:tartaric acid hydroxycinnamoyl transferase activity and accumulate hydroxycinnamoyl-tartaric acid esters, Planta, (2014), 239:1091-1100.
Sullivan, Michael L. et al., Red Clover HCT2, a Hydroxycinnamoyl-Coenzyme A:Malate Hydroxycinnamoyl Transferase, Plays a Crucial Role in Biosynthesis of Phaselic Acid and Other Hydroxycinnamoyl-Malate Esters in Vivo1[OA], Plant Physiology, (2011), 155:1060-1067.
Sullivan, Michael L. et al., Red clover coumarate 3-hydroxylase (CYP98A44) is capable of hydroxylating p-coumaroyl-shikimate but not p-coumaroylmalate: implications for the biosynthesis of phaselic acid, Planta, (2010), 231:319-328.
Medicago truncatula hydroxycinnamoyl transferase with Gen Bank accession No. XM_003598989.2, published Aug. 25, 2015.

* cited by examiner

Primary Examiner — Bratislav Stankovic
(74) Attorney, Agent, or Firm — John Fado; Ariel Atkinson

(57) ABSTRACT

Two novel cDNAs for two different genes, HDT1 and HDT2, are isolated from red clover and sequenced. Both HDT1 and HDT2 encode hydroxycinnamoyl-CoA:L-DOPA/tyrosine hydroxycinnamoyl transferase (HDT) which enzymatically produces clovamide and/or related hydroxycinnamoyl amides. Clovamide and related hydroxycinnamoyl amides reduce post-harvest protein degradation. Genetically altered alfalfa plants containing an expression cassette containing a cDNA encoding HDT1 or HDT2 are generated. These genetically altered alfalfa plants produce hydroxycinnamoyl-CoA:L-DOPA/tyrosine hydroxycinnamoyl transferase, which in turn produces clovamide and/or related hydroxycinnamoyl amides.

4 Claims, 5 Drawing Sheets

Specification includes a Sequence Listing.

FIG. 1A

```
HDT1 (SEQ ID NO. 1)  CAACACAGAACTTCAAGCTAGCATACCAAAAAAAAAAAAATGGTAACCATTATAGCTTCTC 60
HDT2 (SEQ ID NO. 3)  CAACACAGAACTTCAAGCTAGCATACCAAAAAAAAAAAAATGGTAACCATTATAGCTTCTC 60

HDT1 (SEQ ID NO. 1)  ACACTGTGATTCCAGAAGAACCAACTCCACAAGGTCCATTTTGGCTCTCTGATATGGATC 120
HDT2 (SEQ ID NO. 3)  ACACTGTGATTCCAGAAGAACCAACTCCACAAGGTCCATTTTGGCTCTCTGATATGGATC 120

HDT1 (SEQ ID NO. 1)  AAGTGGTTCGTATCCGCGACGTACCAACTCTTTACATTTACAAAACACCAAAGAAAAACC 180
HDT2 (SEQ ID NO. 3)  AAGTGGTTCGTATCCGCGACGTACCAACTCTTTACATTTACAAAACACCAAAGAAAAACC 180

HDT1 (SEQ ID NO. 1)  AAGAAAACAAAAACATAGTAGAAACCTTTAAAAACTCTCTAAGCAAAATTCTTGTTCACT 240
HDT2 (SEQ ID NO. 3)  AAGAAAACAAAAACATAGTAGAAACCTTTAAAAACTCTCTAAGCAAAATTCTTGTTCACT 240

HDT2 (SEQ ID NO. 1)  ACTATCCTATAGCTGGTAGATTGTGTTACATAGAAGGTGGTAGATTAGAATTGAATCTCA 300
HDT1 (SEQ ID NO. 3)  ACTATCCTATAGCTGGTAGATTGTGTTACATAGAAGGTGGTAGATTAGAATTGAATCTCA 300

HDT1 (SEQ ID NO. 1)  ATGCAAAAGGAGCTATTTTGGTTGAAGCTGAAACAGAAAAAACAATGAATGATTATGGTG 360
HDT2 (SEQ ID NO. 3)  ATGCAAAAGGAGCTATTTTGGTTGAAGCTGAAACAGAAAAAACAATGAATGATTATGGTG 360

HDT1 (SEQ ID NO. 1)  ACTTTTCACATTTTGACACCATCAAAGAACTTGTTCCAATGATTGATTACAATCAACCAA 420
HDT2 (SEQ ID NO. 3)  ACTTTTCACATTTTGACACCATCAAAGAACTTGTTCCAATGATTGATTACAATCAACCAA 420

HDT1 (SEQ ID NO. 1)  TTGAAGAAATTCCAAATTTTGTTGTGCAACTCACAAATTTCAAAAACAATGAAGGCTTTG 480
HDT2 (SEQ ID NO. 3)  TTGAAGAAATTCCAAATTTTGTTGTGCAACTCACCAAGTTCAAAAACAATGAAGGCTTTG 480

HDT1 (SEQ ID NO. 1)  CAATTGGTGTTGCTTTTCTCCATCCTTTATCAGATGGATTGGGAGCCATTAAATTCATCA 540
HDT2 (SEQ ID NO. 3)  CAATTGGTGTTGCTTTTCTCCATCCTTTATCAGATGGATTGGGAGCCATTAAATTCATCA 540

HDT1 (SEQ ID NO. 1)  ACTCATGGGCCAAAATAGCAAGAGGTGAAACACTTGAGGCTAATGAGTTACCATTTTTGG 600
HDT2 (SEQ ID NO. 3)  ACTCATGGGCCAAAATAGCAAGAGGTGAAACACTTGAGGCTAATGAGTTACCATTTTTGG 600

HDT1 (SEQ ID NO. 1)  ATAGAAAACTTCTCAAATTTTCACACACACCTTTGGAGCCACGTTTTGAACACTTGGAGT 660
HDT2 (SEQ ID NO. 3)  ATAGAAAACTTCTCAAATTTTCACACACACCTTTGGAGCCACGTTTTGAACACTTGGAGT 660

HDT1 (SEQ ID NO. 1)  TGAAGCCACTACCACTCATTCTAGGTAGAAAAGATGCAAGTGAAGAAAAAGAGAAGAAAA 720
HDT2 (SEQ ID NO. 3)  TGAAGCCACTACCACTCATTCTAGGTAGAAAAGATGCAAGTGAAGAAAAAGAGAAGAAAA 720

HDT1 (SEQ ID NO. 1)  CTTCAGCAACATTGTTGAAACTTTCATCAGAACAAGTTGATAAGTTGAAGAAAAAAGCCA 780
HDT2 (SEQ ID NO. 3)  CTTCAGCAACATTGTTGAAACTTTCATCAGAACAAGTTGATAAGTTAAAGAAAAAAGCCA 780

HDT1 (SEQ ID NO. 1)  ATGAAGAAGATGTTCTAGGTATCCAGAAAAAAGAGTACTCAAGGCCTTATAGTAAATTTG 840
HDT2 (SEQ ID NO. 3)  ATGAAGAAGATGTTCTAGGTGTCCAGAAAAAAGAGTACTCAAGGCCTTATAGTAAATTTG 840

HDT1 (SEQ ID NO. 1)  AAGTAATTAGTGCACATATATGGAGATGTGCATCTAAGGCACGTGAGCTTGAAGATAATC 900
HDT2 (SEQ ID NO. 3)  AAGTAATTAGTGCACATATATGGAGATGTGCATCTAAGGCACGTGAGCTTAAAGATAATC 900

HDT1 (SEQ ID NO. 1)  AAGAAAGTGTTATTAGATTCATTGCTGATGTTAAAAATAGAATGATTCCACCACTTCCTA 960
HDT2 (SEQ ID NO. 3)  AAGAAAGTGTTATTAGATTTATTGCTGATGTTAAAAATAGAATGATTCCACCACTTCCTA 960

HDT1 (SEQ ID NO. 1)  AAAACTATTTTGGGAATGCTTTGACTCAAACAGCTACTAAAGGGTATATTGGAGAAATCA 1020
HDT2 (SEQ ID NO. 3)  AAAACTATTTTGGGAATGCTTTGACTCAAACAGCTACTAAAGGGTATATTGGAGAAATCA 1020

HDT1 (SEQ ID NO. 1)  CATCAAAGCCTTTGGGTTACGTGGCACAAAAGATAAGGGAAGCAACTGAGTTCATAAATG 1080
HDT2 (SEQ ID NO. 3)  CATCAAAGCCTTTAGGTTACGTGGCACAAAAGATAAGGGAAGCAACTGAGTTCGTAAATG 1080

HDT1 (SEQ ID NO. 1)  ATGAGTATATAAGGTCACAAATTGATGTTGTTAGAAGTTTTGAACATTTGGATGATGCAC 1140
HDT2 (SEQ ID NO. 3)  ATGAGTATATAAGGTCACAAATTGATGTTGTTAGAAGTTTTGAACATTTGGATGATGCAC 1140
```

FIG. 1B

```
HDT1 (SEQ ID NO. 1) GAAAAATGTTTATAGGTGAAAAGGCTCGATATTTTGGTAATCCAAATTTTAATTTGACTA 1200
HDT2 (SEQ ID NO. 3) GAAAAATGTTTATAGGTGAAAAGGCTCGATATTTTGGTAATCCAAATTTTAATTTGACTA 1200

HDT1 (SEQ ID NO. 1) GTTGGTTAAGTATGCCTGTTTATGAAGCTGATTTTGGATGGGGGAAACCTAATTACTTTG 1260
HDT2 (SEQ ID NO. 3) GTTGGTTAAGTATGCCTGTTTATGAAGCTGATTTTGGATGGGGTAAACCTAATTACTTTG 1260

HDT1 (SEQ ID NO. 1) GATTAGCTGATGTCTCACCACATGATAGAGCAGTCATTCTTCTTAGTCCTGATGATGATG 1320
HDT2 (SEQ ID NO. 3) GATTAGCTGATGTCTCACCACATGATAGAGCTGTCATTCTTCTTAGTCCTGATGATGATG 1320

HDT1 (SEQ ID NO. 1) GATCTGTTCTTGTGTCTTTCCATTTTCAGATTGCACATATGGAGCTTTTCAACAAGTATT 1380
HDT2 (SEQ ID NO. 3) GATCTGTTCTTGTGTCTTTCCATCTTCAGATTGCACATATGGAGCTTTTCAACAAGTATT 1380

HDT1 (SEQ ID NO. 1) TTTATGAGGAGATATGAAATAGGGGTGGTTTTTGGGTCAATTTTTGACCCAAAATCACCC 1440
HDT2 (SEQ ID NO. 3) TTTATGAGGAGATATGAAATAAGGGTGGTTTTTGGGTCAATTTTTGACCCAAAATCACCC 1440

HDT1 (SEQ ID NO. 1) TCTAAGTTGGT                                                   1451
HDT2 (SEQ ID NO. 3) TCTAAGTTGGT                                                   1451
```

FIG. 2

```
HDT1 (SEQ ID NO. 2)  MVTIIASHTVIPEEPTPQGPFWLSDMDQVVRIRDVPTLYIYKTPKKNQENKNIVETFKNS  60
HDT2 (SEQ ID NO. 4)  MVTIIASHTVIPEEPTPQGPFWLSDMDQVVRIRDVPTLYIYKTPKKNQENKNIVETFKNS  60

HDT1 (SEQ ID NO. 2)  LSXILVHYYPIAGRLCYIEGGRLELNLNAKGAILVEAETEKTMNDYGDFSHFDTIKELVP  120
HDT2 (SEQ ID NO. 4)  LSXILVHYYPIAGRLCYIEGGRLELNLNAKGAILVEAETEKTMNDYGDFSHFDTIKELVP  120

HDT1 (SEQ ID NO. 2)  MIDYNQPIEEIPNFVVQLTNFKNNEGFAIGVAFLHPLSDGLGAIKFINSWAKIARGETLE  180
HDT2 (SEQ ID NO. 4)  MIDYNQPIEEIPNFVVQLTKFKNNEGFAIGVAFLHPLSDGLGAIKFINSWAKIARGETLE  180

HDT1 (SEQ ID NO. 2)  ANELPFLDRKLLKFSHTPLEPRFEHLELKPLPLILGRKDASEEKEKKTSATLLKLSSEQV  240
HDT2 (SEQ ID NO. 4)  ANELPFLDRKLLKFSHTPLEPRFEHLELKPLPLILGRKDASEEKEKKTSATLLKLSSEQV  240

HDT1 (SEQ ID NO. 2)  DKLKKKANEEDVLGTQKKEYSRPYSKFEVISAHIWRCASKARELEDNQESVIRFIADVKN  300
HDT2 (SEQ ID NO. 4)  DKLKKKANEEDVLGVQKKEYSRPYSKFEVISAHIWRCASKARELKDNQESVIRFIADVKN  300

HDT1 (SEQ ID NO. 2)  RMIPPLPKNYFGNALTQTATKGYIGEITSKPLGYVAQKIREATELTNDEYIRSQIDVVRS  360
HDT2 (SEQ ID NO. 4)  RMIPPLPKNYFGNALTQTATKGYIGEITSKPLGYVAQKIREATELMNDEYIRSQIDVVRS  360

HDT1 (SEQ ID NO. 2)  FEHLDDARKMFIGEKARYFGNPNFNLTSWLSMPVYEADFGWGKPNYFGLADVSPHDRAVI  420
HDT2 (SEQ ID NO. 4)  FEHLDDARKMFIGEKARYFGNPNFNLTSWLSMPVYEADFGWGKPNYFGLADVSPHDRAVI  420

HDT1 (SEQ ID NO. 2)  LLSPDDDGSVLVSFHFQIAHMELFNKYFYEEI                             452
HDT2 (SEQ ID NO. 4)  LLSPDDDGSVLVSFHLQIAHMELFNKYFYEEI                             452
```

FIG. 3

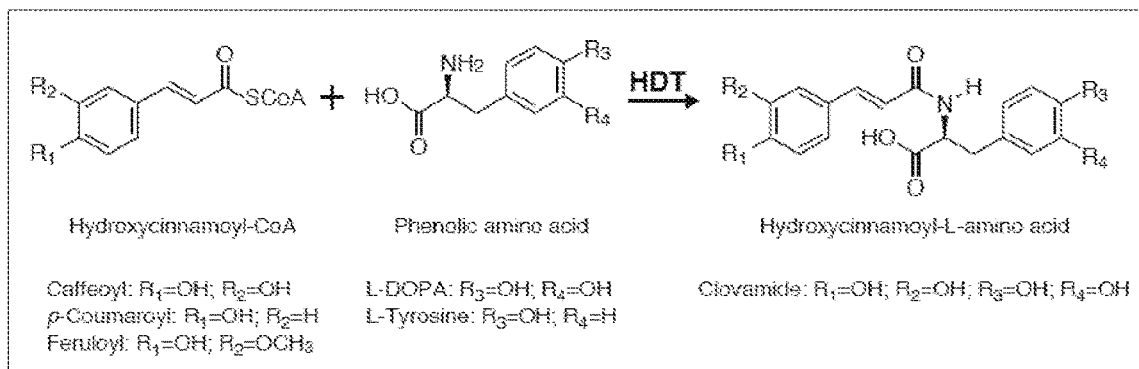

Retention time (min)

Retention time (min)

US 10,711,278 B2

GENETICALLY ALTERED ALFALFA PRODUCING CLOVAMIDE AND/OR RELATED HYDROXYCINNAMOYL AMIDES

CROSS-REFERENCE TO RELATED APPLICATIONS

This application is a divisional application of U.S. patent application Ser. No. 15/274,050 filed on Sep. 23, 2016 (allowed) which claims priority to U.S. patent application Ser. No. 62/234,720 filed on Sep. 30, 2015, the contents of each of which is hereby incorporated by reference in their entirety.

SEQUENCE LISTING

The Sequence Listing submitted via EFS-Web as ASCII compliant text file format (.txt) filed on Sep. 23, 2016, named "SequenceListing_ST25", (created on Sep. 13, 2016, 15 KB), is incorporated herein by reference. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

BACKGROUND OF THE INVENTION

Field of the Invention

This invention relates genetically altered alfalfa plants that contain heterologous cDNA encoding hydroxycinnamoyl-CoA:L-DOPA/tyrosine hydroxycinnamoyl transferase (HDT) and produce clovamide and/or related hydroxycinnamoyl amides. This invention also relates to the cDNAs that encode HDT1 and HDT2 obtained from red clover, expression vectors containing the cDNAs, and the use of the cDNAs and/or expression vectors to genetically modify alfalfa so that the modified alfalfa can produce clovamide and/or related hydroxycinnamoyl amides. This invention also relates to genetically altered alfalfa that have a phenotype involving post-harvest protein protection.

Description of Related Art

Clovamide (an amide formed between caffeic acid and L-DOPA [L-3,4-dihydroxyphenylalanine]) is one of two major o-diphenol compounds present in leaves of red clover. The other major o-diphenol compound present in red clover leaves is phaselic acid (an ester formed between caffeic acid and malic acid). When oxidized by the endogenous polyphenol oxidase system (PPO), caffeic acid derivatives such as phaselic acid and clovamide constitute a natural system of post-harvest protein protection for forage crops. See U.S. Pat. No. 8,338,339.

Unfortunately, many important forages, like alfalfa, do not make PPO or the o-diphenol compounds needed for this process. For alfalfa alone, post-harvest proteolytic losses upon harvest and storage as silage cost U.S. farmers an estimated $100 million annually. Poor utilization of degraded forage protein by ruminant animals also results in release of the excess nitrogen into the environment as urea. Forages rich in PPO and o-diphenols appear to have reduced protein and lipid degradation in the rumen, with the potential for additional nitrogen utilization efficiency and improved lipid profiles of animal products, respectively (see, Lee et al., 2004, *J. Sci. Food Agric.* 84:1639).

Mature red clover leaves accumulate relatively high levels of two caffeic acid derivatives: phaselic acid (an ester formed between caffeic acid and malic acid) (5 to 8 mmol/kg fresh weight [FW]), and clovamide (an amide formed between caffeic acid and the amino acid L-DOPA) (3 to 6 mmol/kg FW) (Sullivan and Zeller, 2013, *J. Sci. Food. Agri.* 93(2):219-26). Previously, a red clover gene (HCT2, Genbank EU861219) encoding a hydroxycinnamoyl-CoA: malate hydroxycinnamoyl transferase (HMT) was shown to be crucial for phaselic acid accumulation in red clover leaves (Sullivan and Zarnowski, 2011, *Plant Physiol.* 155 (3):1060-7).

Although in red clover, phaselic acid is a major hydroxycinnamoyl-malate ester, expression of red clover HCT2 in alfalfa results in mostly accumulation of p-coumaroyl-malate and feruloyl-malate, compounds that do not function with PPO to preserve forage protein. See, Sullivan, M., (2015) "Engineering alfalfa to accumulate useful caffeic acid derivatives and characterization of hydroxycinnamoyl-CoA transferases from legumes" in The Phytochemical Society of North America, Aug. 8-12, 2015 (conferences.illinois.edu/psna/documents/ PSNA_2015_Full_Program.pdf). This accumulation pattern in alfalfa is actually consistent with the in-vitro enzymatic properties of HCT2 gene product (HMT) whereby p-coumaroyl-CoA and feruloyl-CoA donor substrates are preferred over caffeoyl-CoA by five- to tenfold (see Sullivan and Zarnowski, 2011).

Thus, a need exists for genetically altered alfalfa plants that can produce clovamide and/or related hydroxycinnamoyl amides which can protect proteins from post-harvest degradation. Such a genetically altered alfalfa plant must contain cDNA encoding the appropriate enzyme which produces clovamide. Based on the research presented below, that enzyme is termed hydroxycinnamoyl-CoA:L-DOPA/ tyrosine hydroxycinnamoyl transferase (HDT).

BRIEF SUMMARY OF THE INVENTION

It is an object of this invention to have two novel and isolated cDNAs, each encoding an enzyme having hydroxycinnamoyl-CoA:L-DOPA/tyrosine hydroxycinnamoyl transferase (HDT) activity. It is another object of this invention that the cDNA for HDT1 has the sequence of SEQ ID NO: 1 or a sequence that is at least 95% identical to SEQ ID NO: 1. It is another object of this invention that the cDNA for HDT2 has the sequence of SEQ ID NO: 3 or a sequence that is at least 95% identical to SEQ ID NO: 3. It is a further object of this invention to have expression cassettes containing a promoter operably linked to one of these cDNAs. The promoter can be constitutive, inducible, or tissue specific.

It is a further object of this invention to have two novel proteins, hydroxycinnamoyl-CoA:L-DOPA/tyrosine hydroxycinnamoyl transferase, referred to as HDT1 and HDT2. The amino acid sequence of HDT1 is SEQ ID NO: 2 or a sequence that is at least 95% identical to SEQ ID NO: 2 (so long as the protein possesses hydroxycinnamoyl-CoA: L-DOPA/tyrosine hydroxycinnamoyl transferase activity). The amino acid sequence of HDT2 is SEQ ID NO: 4 or a sequence that is at least 95% identical to SEQ ID NO: 4 (so long as the protein possesses hydroxycinnamoyl-CoA:L-DOPA/tyrosine hydroxycinnamoyl transferase activity). It is a further object of this invention to have cDNAs that encode HDT1 and HDT2 proteins (or a protein that is at least 95% identical to SEQ ID NO: 2 or SEQ ID NO: 4 and which possess hydroxycinnamoyl-CoA:L-DOPA/tyrosine hydroxycinnamoyl transferase activity). It is another object of this invention to have expression cassettes containing a promoter operably linked to one of these cDNAs that encode HDT1 or HDT2 (or a polynucleotide that encodes a protein that is at least 95% identical to HDT1 or HDT2 and possesses hydroxycinnamoyl-CoA:L-DOPA/tyrosine hydroxycinnamoyl transferase activity). The promoter can be constitutive, inducible, or tissue specific.

It is another object of this invention to have a genetically altered alfalfa plant that has hydroxycinnamoyl-CoA:L-DOPA/tyrosine hydroxycinnamoyl transferase activity, the genetically alfalfa plant contains a promoter operably linked to a heterologous cDNA (an expression cassette) such that the heterologous cDNA encodes a hydroxycinnamoyl-CoA:L-DOPA/tyrosine hydroxycinnamoyl transferase. It is an object of this invention that the encoded protein can be HDT1 (SEQ ID NO: 2), HDT2 (SEQ ID NO: 4), or a protein having an amino acid sequence that is at least 95% to SEQ ID NO: 2 or SEQ ID NO: 4. It is a further object of this invention to have a pollen, seed, or cell from this genetically altered alfalfa plant. It also an object of this invention to have a tissue culture of cells from this genetically altered alfalfa plant.

It is an object of this invention to have a genetically altered alfalfa plant that has hydroxycinnamoyl-CoA:L-DOPA/tyrosine hydroxycinnamoyl transferase activity, the genetically alfalfa plant contains a promoter operably linked to a heterologous cDNA (an expression cassette). It is another object of this invention that the cDNA has a sequence that can be SEQ ID NO: 1, SEQ ID NO: 3, or a sequence that is at least 95% identical to SEQ ID NO: 1 or SEQ ID NO: 3 so long as the encoded protein contains hydroxycinnamoyl-CoA:L-DOPA/tyrosine hydroxycinnamoyl transferase activity. It is a further object of this invention to have a pollen, seed, or cell from this genetically altered alfalfa plant. It also an object of this invention to have a tissue culture of cells from this genetically altered alfalfa plant.

It is an object of this invention to have a method of reducing post-harvest protein degradation in a genetically alfalfa plant by (a) introducing a promoter operably linked to a heterologous cDNA into an alfalfa plant to provide a genetically altered alfalfa plant, such that the heterologous cDNA encodes a hydroxycinnamoyl-CoA:L-DOPA/tyrosine hydroxycinnamoyl transferase which can have an amino acid sequence of SEQ ID NO: 2, SEQ ID NO: 4, a sequence that is at least 95% identical to SEQ ID NO: 2, or a sequence that is at least 95% identical to SEQ ID NO: 4, and (b) selecting the genetically altered alfalfa plant that contains the heterologous cDNA and/or produces protein encoded therein, such that the protein encoded by the heterologous cDNA produced clovamide, at least one related hydroxycinnamoyl amide, or a combination thereof. The clovamide, at least one related hydroxycinnamoyl amide, or combination thereof reduces post-harvest protein degradation in the genetically altered alfalfa. It is a further object of this invention that the step of introducing the heterologous cDNA into the alfalfa plant occurs via introgression, breeding, or transfecting an expression cassette containing the heterologous nucleotide and promoter into the alfalfa plant. It is another object of this invention the step of selecting the genetically altered alfalfa plant occurs via marker assisted selection. It is another object of this invention that marker assisted selection involves using primers having a sequence of SEQ ID NO: 9 and/or SEQ ID NO: 10 in a PCR reaction.

It is another object of this invention to have a method of reducing post-harvest protein degradation in a genetically altered alfalfa plant by (a) introducing a promoter operably linked to a heterologous polynucleotide into an alfalfa plant to provide a genetically altered alfalfa plant, such that the heterologous polynucleotide has the sequence of SEQ ID NO: 1, SEQ ID NO: 3, a sequence that is at least 95% identical to SEQ ID NO: 1, or a sequence that is at least 95% identical to SEQ ID NO: 3, and such that the heterologous polynucleotide encodes a protein having hydroxycinnamoyl-CoA:L-DOPA/tyrosine hydroxycinnamoyl transferase activity, and (b) selecting the genetically altered alfalfa plant that contains the heterologous polynucleotide and/or produces the protein having hydroxycinnamoyl-CoA:L-DOPA/tyrosine hydroxycinnamoyl transferase activity, such that the protein having hydroxycinnamoyl-CoA:L-DOPA/tyrosine hydroxycinnamoyl transferase activity produces clovamide, at least one related hydroxycinnamoyl amide, or a combination thereof. The clovamide, at least one related hydroxycinnamoyl amide, or combination thereof reduces post-harvest protein degradation in the genetically altered alfalfa. It is also an object of the invention that the introducing of the heterologous polynucleotide occurs via introgression, breeding, or transfecting an expression cassette containing the heterologous nucleotide and promoter into the alfalfa plant. It is a further object of the invention that the selecting of the genetically altered alfalfa plant occurs via marker assisted selection. It is another object of this invention that marker assisted selection involves using primers having a sequence of SEQ ID NO: 9 and/or SEQ ID NO: 10 in a PCR reaction.

It is yet another object of this invention to have a method of constructing a genetically altered alfalfa plant that produces clovamide, at least one related hydroxycinnamoyl amide, or a combination thereof by (a) introducing a promoter operably linked to a heterologous cDNA into an alfalfa plant to provide a genetically altered alfalfa plant, such that the heterologous cDNA encodes a hydroxycinnamoyl-CoA:L-DOPA/tyrosine hydroxycinnamoyl transferase having the amino acid sequence of SEQ ID NO: 2, SEQ ID NO: 4, a sequence that is at least 95% identical to SEQ ID NO: 2, or a sequence that is at least 95% identical to SEQ ID NO: 4, and (b) selecting the genetically altered alfalfa plant that contains the heterologous cDNA and/or produces the protein encoded therein. The hydroxycinnamoyl-CoA:L-DOPA/tyrosine hydroxycinnamoyl transferase produces clovamide, at least one related hydroxycinnamoyl amide, or a combination thereof. It is a further object of this invention that the introducing the heterologous cDNA occurs via introgression, breeding, or transfecting an expression cassette containing the heterologous nucleotide and promoter into the alfalfa plant. It is yet another object of this invention that the selecting of the genetically altered alfalfa plant occurs via marker assisted selection. It is another object of this invention that marker assisted selection involves using primers having a sequence of SEQ ID NO: 9 and/or SEQ ID NO: 10 in a PCR reaction.

It is yet a further object of this invention to have a method of constructing a genetically altered alfalfa plant that produces clovamide, at least one related hydroxycinnamoyl amide, or a combination thereof by (a) introducing a promoter operably linked to a heterologous polynucleotide into an alfalfa plant to provide the genetically altered alfalfa plant, such that the heterologous polynucleotide has the sequence of SEQ ID NO: 1, SEQ ID NO: 3, a sequence that is at least 95% identical to SEQ ID NO: 1, or a sequence that is at least 95% identical to SEQ ID NO: 3, and such that the heterologous polynucleotide encodes a protein having hydroxycinnamoyl-CoA:L-DOPA/tyrosine hydroxycinnamoyl transferase activity, and (b) selecting the genetically altered alfalfa plant that contains the heterologous polynucleotide and/or produces the protein encoded thereby and the protein having hydroxycinnamoyl-CoA:L-DOPA/tyrosine hydroxycinnamoyl transferase produces clovamide, at least one related hydroxycinnamoyl amide, or a combination thereof. It is an object of this invention that the introducing the heterologous polynucleotide occurs via introgression, breeding, or transfecting an expression cassette containing the promoter and heterologous nucleotide into the alfalfa plant. It is yet another object of this invention that the selecting of the genetically altered alfalfa plant occurs via marker assisted selection. It is another object of this invention that marker assisted selection involves using primers having a sequence of SEQ ID NO: 9 and/or SEQ ID NO: 10 in a PCR reaction.

It is another object of this invention to have a kit for determining if an alfalfa plant contains cDNA for HDT1 or HDT2 and thereby produces a hydroxycinnamoyl-CoA:L-DOPA/tyrosine hydroxycinnamoyl transferase. This kit contains at least one pair of polynucleotides; an identifying dye; and instructions for using the at least one pair of polynucleotides, such that the pair of polynucleotides have the sequence of SEQ ID NO: 9 and SEQ ID NO: 10, respectively; and such that if the alfalfa plant possesses the polynucleotide sequence of SEQ ID NO: 9 or SEQ ID NO: 10, then the alfalfa plant contains either the HDT1 or HDT2 gene.

BRIEF DESCRIPTION OF THE FIGURES

FIG. 1A and FIG. 1B show the sequence alignment of HDT1 (SEQ ID NO: 1) and HDT2 (SEQ ID NO: 3). ATG and TGA codons are bolded and underlined. The non-identical nucleotides are highlighted in black.

FIG. 2 is sequence alignment of HDT1 (SEQ ID NO: 2) and HDT2 (SEQ ID NO: 4) with the non-identical amino acids highlighted in black.

FIG. 3 shows the enzymatic reaction of a hydroxycinnamoyl-Coenzyme A compound and a phenolic amino acid compound by hydroxycinnamoyl-CoA:L-DOPA/tyrosine hydroxycinnamoyl transferase (HDT) to produce clovamide (hydroxycinnamoyl-L-DOPA) and/or related hydroxycinnamoyl compounds.

DETAILED DESCRIPTION OF THE INVENTION

Figure 4A:
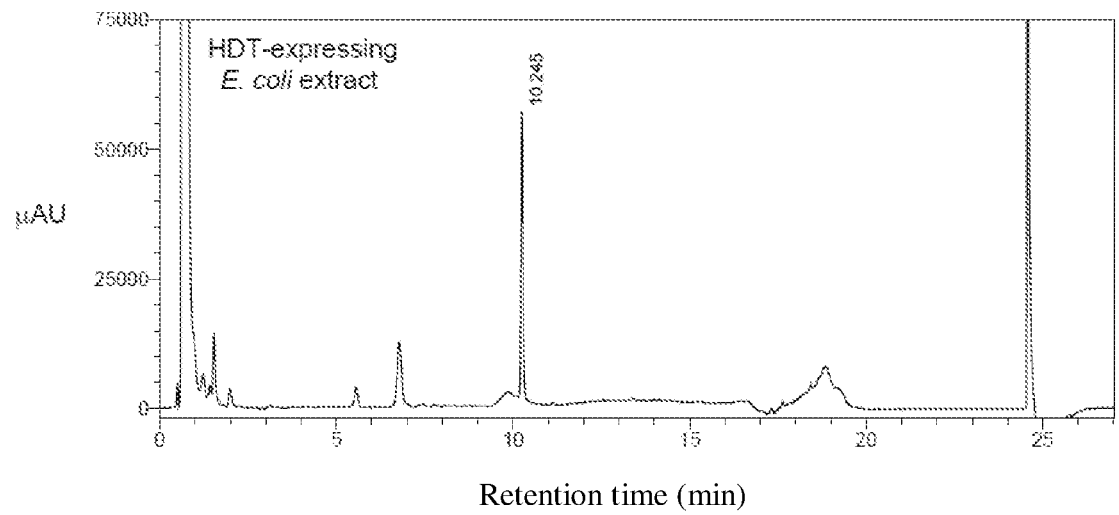
FIG. 4A demonstrates that E. coli BL21/pET28-HDT1 possesses hydroxycinnamoyl-CoA transferase activity via the reverse phase HPLC of the in-vitro reaction of E. coli BL21/pET28-HDT1 extract with caffeoyl-CoA donor substrate and L-DOPA acceptor substrate which produces a peak at approximately 10.245 minutes which is clovamide.

The previously published data described above led to the hunt for the gene that encodes an enzyme that produces clovamide in red clover and will produce clovamide in genetically altered alfalfa. This enzyme is distinct from HMT (encoded by HCT2) (Sullivan, 2009, *Plant Physiol.* 150:1866-1879). Using PCR, two novel red clover cDNAs (HDT1 (SEQ ID NO: 1) and HDT2 (SEQ ID NO: 3)) encoding HDT1 (SEQ ID NO: 2) and HDT2 (SEQ ID NO: 4), respectively, are isolated and sequenced. See FIGS. 1A, 1B, 2A, and 2B. The encoded enzymes, hydroxycinnamoyl-CoA:L-DOPA/tyrosine hydroxycinnamoyl transferase 1 and hydroxycinnamoyl-CoA:L-DOPA/tyrosine hydroxycinnamoyl transferase 2, are enzymatically active, contain 452 amino acids and differ by 5 amino acids—at positions 140, 255, 285, 346, and 436. The cDNAs HDT1 and HDT2 are each 1451 nucleotides long and differ by 12 nucleotides—at positions 455, 458, 767, 801, 891, 920, 1034, 1074, 1244, 1292, 1344, and 1402. See FIG. 1A, FIG. 1B for cDNA sequence alignment, and FIG. 2 for amino acid sequence alignment. When genetically altered alfalfa are generated containing either HDT1 or HDT2, the genetically altered alfalfa produce a protein having hydroxycinnamoyl-CoA:L-DOPA/tyrosine hydroxycinnamoyl transferase and can produce clovamide and/or other related hydroxycinnamoyl amides. Thus, these genetically altered alfalfa plants have the reduced post-harvest degradation of proteins which improve the nutritional value of the genetically altered alfalfa.

The term "related hydroxycinnamoyl amides" refers to other compounds produced by HDT1 and/or HDT2 (a protein having hydroxycinnamoyl-CoA:L-DOPA/tyrosine hydroxycinnamoyl transferase) and which reduce post-harvest degradation of proteins in plant containing the related hydroxycinnamoyl amides (genetically altered alfalfa, red clover, etc.). These related hydroxycinnamoyl amides can be, but are not limited to, N-caffeoyl-L-tyrosine, N-p-coumaroyl-L-3,4-dihydroxyphenylalanine (also called N-p-coumaroyl-L-DOPA), and N-feruloyl-L-3,4-dihydroxyphenylalanine (also called N-feruloyl-L-DOPA). Clovamide is also referred to as N-caffeoyl-L-3,4-dihydroxyphenylalanine or N-caffeoyl-L-DOPA.

Because this invention involves production of genetically altered plants and involves recombinant DNA techniques, the following definitions are provided to assist in describing this invention. The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term "purified" denotes that a nucleic acid or protein that gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98(1994)). Because the amino acid sequences of SEQ ID NO: 2 and SEQ ID NO: 4 are described herein, one can chemically synthesize a polynucleotide which encodes these enzymes. Because of the degeneracy of nucleic acid codons, one can use various different polynucleotides to encode identical proteins. Table 1, infra, contains information about which nucleic acid codons encode which amino acids.

properties of the reference protein. In other words, conservative amino acid substitutions substantially conserve the structure and the function of the reference protein. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, can also be expected to produce a functionally equivalent protein or polypeptide. Table 2 provides a list of exemplary conservative amino acid substitutions. Conservative amino acid substitutions generally maintain (a) the structure of the protein backbone in the area of the substitution, for example, as a beta sheet or alpha helical conformation, (b) the charge or hydrophobicity of the molecule at the site of the substitution, and/or (c) the bulk of the side chain.

TABLE 2

| Amino Acid | Conservative Substitute |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Ile, Leu |

TABLE 1

| Amino acid | Nucleic acid codons | Amino acid | Nucleic acid codons |
|---|---|---|---|
| Ala/A | GCT, GCC, GCA, GCG | Leu/L | TTA, TTG, CTT, CTC, CTA, CTG |
| Arg/R | CGT, CGC, CGA, CGG, AGA, AGG | Lys/K | AAA, AAG |
| Asn/N | AAT, AAC | Met/M | ATG |
| Asp/D | GAT, GAC | Phe/F | TTT, TTC |
| Cys/C | TGT, TGC | Pro/P | CCT, CCC, CCA, CCG |
| Gln/Q | CAA, CAG | Ser/S | TCT, TCC, TCA, TCG, AGT, AGC |
| Glu/E | GAA, GAG | Thr/T | ACT, ACC, ACA, ACG |
| Gly/G | GGT, GGC, GGA, GGG | Trp/W | TGG |
| His/H | CAT, CAC | Tyr/Y | TAT, TAC |
| Ile/I | ATT, ATC, ATA | Val/V | GTT, GTC, GTA, GTG |

In addition to the degenerate nature of the nucleotide codons which encode amino acids, alterations in a polynucleotide that result in the production of a chemically equivalent amino acid at a given site, but do not affect the functional properties of the encoded protein, are well known in the art. "Conservative amino acid substitutions" are those substitutions that are predicted to interfere least with the TABLE 2-continued

| Amino Acid | Conservative Substitute |
|---|---|
| Phe | His, Leu, Met, Trp, Tyr |
| Ser | Cys, Thr |
| Thr | Ser, Val |

TABLE 2-continued

| Amino Acid | Conservative Substitute |
| --- | --- |
| Trp | Phe, Tyr |
| Tyr | His, Phe, Trp |
| Val | Ile, Leu, Thr |

Oligonucleotides and polynucleotides that are not commercially available can be chemically synthesized e.g., according to the solid phase phosphoramidite triester method first described by Beaucage and Caruthers, *Tetrahedron Letts.* 22:1859-1862 (1981), or using an automated synthesizer, as described in Van Devanter et al., *Nucleic Acids Res.* 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, *J. Chrom.* 255:137-149 (1983).

The terms "identical" or percent "identity", in the context of two or more nucleic acids or polypeptide sequences, refer to two or more sequences or subsequences that are the same or have a specified percentage of amino acid residues or nucleotides that are the same (e.g., 80%, 85% identity, 90% identity, 99%, or 100% identity), when compared and aligned for maximum correspondence over a designated region as measured using a sequence comparison algorithm or by manual alignment and visual inspection.

The phrase "high percent identical" or "high percent identity", in the context of two polynucleotides or polypeptides, refers to two or more sequences or subsequences that have at least about 80%, identity, at least about 81%, 82%, 83%, 84%, 85%, 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, a high percent identity exists over a region of the sequences that is at least about 50 residues in length. In another exemplary embodiment, a high percent identity exists over a region of the sequences that is at least about 100 residues in length. In still another exemplary embodiment, a high percent identity exists over a region of the sequences that is at least about 150 residues or more in length. In one exemplary embodiment, the sequences are high percent identical over the entire length of the nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al. (eds.), *Current Protocols in Molecular Biology*, 1995 supplement).

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes that are not found within the native (non-recombinant or wild-type) form of the cell or express native genes that are otherwise abnormally expressed—over-expressed, under-expressed or not expressed at all.

The terms "transgenic", "transformed", "transformation", and "transfection" are similar in meaning to "recombinant". "Transformation", "transgenic", and "transfection" refer to the transfer of a polynucleotide into the genome of a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed into a cell but are not integrated into the host's chromosome remain as an expression vector within the cell. One may need to grow the cell under certain growth or environmental conditions in order for the expression vector to remain in the cell or the cell's progeny. Further, for expression to occur the organism or cell may need to be kept under certain conditions. Host organisms or cells containing the recombinant polynucleotide can be referred to as "transgenic" or "transformed" organisms or cells or simply as "transformants", as well as recombinant organisms or cells.

A genetically altered organism is any organism with any change to its genetic material, whether in the nucleus or cytoplasm (organelle). As such, a genetically altered organism can be a recombinant or transformed organism. A genetically altered organism can also be an organism that was subjected to one or more mutagens or the progeny of an organism that was subjected to one or more mutagens and has changes in its DNA caused by the one or more mutagens, as compared to the wild-type organism (i.e, organism not subjected to the mutagens). Also, an organism that has been bred to incorporate a mutation into its genetic material is a genetically altered organism. For the purposes of this invention, the organism is a plant.

The term "vector" refers to some means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature; etc. There are various types of vectors including virus, plasmid, bacteriophages, cosmids, and bacteria.

An expression vector is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette". In contrast, as described in the examples herein, a "cassette" is a polynucleotide containing a section of an expression vector of this invention. The use of the cassettes assists in the assembly of the expression vectors. An expression vector is a replicon, such as plasmid, phage, virus, chimeric virus, or cosmid, and which contains the expression control sequence(s) operably linked to the desired polynucleotide sequence.

A polynucleotide sequence is operably linked to an expression control sequence(s) (e.g., a promoter and, optionally, an enhancer) when the expression control sequence controls and regulates the transcription and/or translation of that polynucleotide sequence.

As used herein, the term "promoter" refers to a polynucleotide that in its native state is located upstream or 5' to a translational start codon of an open reading frame (or protein-coding region) and that is involved in recognition and binding of RNA polymerase and other proteins (trans-acting transcription factors) to initiate transcription. A "plant promoter" is a native or non-native promoter that is functional in plant cells. The promoters that predominately function in particular cells and/or tissue are considered "tissue-specific promoters". A plant promoter can be used as a 5' regulatory element for modulating expression of a particular desired polynucleotide (heterologous polynucleotide) operably linked thereto. When operably linked to a transcribeable polynucleotide, a promoter typically causes the transcribable polynucleotide to be transcribed in a manner that is similar to that of which the promoter is normally associated. This transcribeable polynucleotide can be heterologous to the promoter, or heterologous to the organism into which the cassette will be transfected, or both.

A heterologous polynucleotide sequence is operably linked to one or more transcription regulatory elements (e.g., promoter, terminator and, optionally, enhancer) such that the transcription regulatory elements control and regulate the transcription and/or translation of that heterologous polynucleotide sequence. A cassette can have the heterologous polynucleotide operably linked to one or more transcription regulatory elements. As used herein, the term "operably linked" refers to a first polynucleotide, such as a promoter, connected with a second transcribable polynucleotide, such as a gene of interest, where the polynucleotides are arranged such that the first polynucleotide affects the transcription of the second polynucleotide. In some embodiments, the two polynucleotide molecules are part of a single contiguous polynucleotide. In other embodiments, the two polynucleotides are adjacent. For example, a promoter is operably linked to a gene of interest if the promoter regulates or mediates transcription of the gene of interest in a cell. Similarly a terminator is operably linked to the polynucleotide of interest if the terminator regulates or mediates transcription of the polynucleotide of interest, and in particular, the termination of transcription. Constructs of the present invention would typically contain a promoter operably linked to a transcribable polynucleotide operably linked to a terminator.

Exemplary heterologous polynucleotide for incorporation into constructs of the present invention include, for example, desired polynucleotides from a species other than the target plant's species, or even desired polynucleotides that originate with or are present in the same plant species, but are incorporated into the genetically altered plant cells by genetic engineering methods rather than classical reproduction or breeding techniques or by a combination of genetic engineering methods followed by breeding techniques. Heterologous polynucleotides refer to any polynucleotide molecule that is introduced into a recipient cell and is transcribed at levels that differ from the wild-type cell. A heterologous polynucleotide can include a polynucleotide that is already present in the plant cell, polynucleotide from another plant, polynucleotide from a different organism, or a polynucleotide generated externally, such as a polynucleotide containing an antisense message of a gene, or a polynucleotide encoding an artificial or modified version of a gene.

Transformation and generation of genetically altered monocotyledonous and dicotyledonous plant cells is well known in the art. See, e.g., Weising, et al., *Ann. Rev. Genet.* 22:421-477 (1988); U.S. Pat. No. 5,679,558; *Agrobacterium Protocols*, ed: Gartland, Humana Press Inc. (1995); and Wang, et al. *Acta Hort.* 461:401-408 (1998). The choice of method varies with the type of plant to be transformed, the particular application and/or the desired result. The appropriate transformation technique is readily chosen by the skilled practitioner.

Exemplary transformation/transfection methods available to those skilled in the art include, but are not limited to: direct uptake of foreign DNA constructs (see, e.g., EP 295959); techniques of electroporation (see, e.g., Fromm et al., *Nature* 319:791 (1986)); and high-velocity ballistic bombardment with metal particles coated with the nucleic acid constructs (see, e.g., Kline, et al., *Nature* 327:70 (1987) and U.S. Pat. No. 4,945,050). Specific methods to transform heterologous genes into commercially important crops (to make genetically altered plants) are published for rapeseed (De Block, et al., *Plant Physiol.* 91:694-701 (1989)); sunflower (Everett, et al., *Bio/Technology* 5:1201 (1987)); soybean (McCabe, et al., *Bio/Technology* 6:923 (1988), Hinchee, et al., *Bio/Technology* 6:915 (1988), Chee, et al., *Plant Physiol.* 91:1212-1218 (1989), and Christou, et al., *Proc. Natl. Acad. Sci USA* 86:7500-7504 (1989)); rice (Hiei, et al., *Plant J.* 6:271-282 (1994)), and corn (Gordon-Kamm, et al., *Plant Cell* 2:603-618 (1990), and Fromm, et al., *Biotechnology* 8:833-839 (1990)). Other known methods are disclosed in U.S. Pat. Nos. 5,597,945; 5,589,615; 5,750,871; 5,268,526; 5,262,316; and 5,569,831.

One exemplary method includes employing *Agrobacterium tumefaciens* or *Agrobacterium rhizogenes* as the transforming agent to transfer heterologous DNA into the plant. *Agrobacterium tumefaciens*-meditated transformation techniques are well described in the scientific literature. See, e.g., Horsch, et al. *Science* 233:496-498 (1984), and Fraley, et al. *Proc. Natl. Acad. Sci. USA* 80:4803 (1983). Typically, a plant cell, an explant, a meristem or a seed is infected with *Agrobacterium tumefaciens* transformed with the expression vector/construct which contains a promoter operably linked to the heterologous nucleic acid. Under appropriate conditions known in the art, the transformed plant cells are grown to form shoots, roots, and develop further into genetically altered plants. In some embodiments, the heterologous nucleic acid can be introduced into plant cells, by means of the Ti plasmid of *Agrobacterium tumefaciens*. The Ti plasmid is transmitted to plant cells upon infection by *Agrobac-* terium tumefaciens, and is stably integrated into the plant genome. See, e.g., Horsch, et al. (1984), and Fraley, et al. (1983).

Transformed plant cells which are derived by any of the above transformation techniques can be cultured to regenerate a whole plant which possesses the desired transformed phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture*, in *Handbook of Plant Cell Culture*, pp. 124-176, MacMillan Publishing Company, New York, 1983; and Binding, *Regeneration of Plants*, in *Plant Protoplasts*, pp. 21-73, CRC Press, Boca Raton, 1985. Regeneration can also be obtained from plant callus, explants, organs, or parts thereof. Such regeneration techniques are described generally in Klee, et al., *Ann. Rev. of Plant Phys.* 38:467-486 (1987).

Once a genetically altered diploid plant has been generated, one can breed it with a wild-type plant and screen for heterozygous F1 generation diploid plants containing the genetic change present in the parent genetically altered plant. Then F2 generation diploid plants can be generated which are homozygous for the genetic alteration for diploid species. These heterozygous F1 generation plants and homozygous F2 plants, progeny of the original genetically altered plant, are considered genetically altered plants, having the altered genomic material from the genetically altered parent plant. Alfalfa is autotetraploid; thus among F2 plants, some would have two copies of the gene. Generation of F3, and possibly F4 crosses, are required to produce homozygous autoploidy plants.

After one obtains a genetically altered plant expressing the heterologous protein, one can efficiently breed the genetically altered plant with other plants containing desired traits. One can use molecular markers (i.e., polynucleotide probes) based on the sequence of the heterologous protein as described above to determine which offspring of crosses between the genetically altered plant and the other plant have the polynucleotide encoding the chimeric protein. This process is known as Marker Assisted Rapid Trait Introgression (MARTI). Briefly, MARTI involves (1) crossing the genetically altered plant with a plant line having desired phenotype/genotype ("elite parent") for introgression to obtain F1 offspring. The F1 generation is heterozygous for chimeric protein trait. (2) Next, an F1 plant is be backcrossed to the elite parent, producing BC1F1 which genetically produces 50% wild-type and 50% heterozygote chimeric protein. (3) PCR using the polynucleotide probe is performed to select the heterozygote genetically altered plants containing polynucleotide encoding the chimeric protein. (4) Selected heterozygotes are then backcrossed to the elite parent to perform further introgression. (5) This process of MARTI is performed for another four cycles. (6) Next, the heterozygote genetically altered plant is self-pollinated by bagging to produce BC6F2 generation. The BC6F2 generation produces a phenotypic segregation ratio of 3 wild-type parent plants to 1 chimeric protein genetically altered plant. (7) One selects genetically altered plants expressing the protein of interest at the BC6F2 generation at the seedling stage using PCR with the polynucleotide probe and can optionally be combined with phenotypic selection at maturity. These cycles of crossing and selection can be achieved in a span of 2 to 2.5 years (depending on the plant), as compared to many more years for conventional backcrossing introgression method now in use. Thus, the application of MARTI using PCR with a polynucleotide probe significantly reduces the time to introgress the chimeric protein genetic alteration into elite lines for producing commercial hybrids. The final product is an inbred plant line almost identical (99%) to the original elite inbred parent plant that is the homozygous for the polynucleotide encoding the chimeric protein. Alternatively, one can apply PCR to one of the methods of breeding alfalfa (described above) to identify those genetically altered alfalfa plants offspring that contain the desired genotype and phenotype. Such an approach is still referred to as MARTI, and introgression still refers to the transferring of a desired genotype/phenotype to the progeny of a cross between alfalfa containing different genotypes/phenotypes.

This invention utilizes routine techniques in the field of molecular biology. Basic texts disclosing the general methods of use in this invention include Green and Sambrook, 4th ed. 2012, Cold Spring Harbor Laboratory; Kriegler, *Gene Transfer and Expression: A Laboratory Manual* (1993); and Ausubel et al., eds., *Current Protocols in Molecular Biology*, 1994-current, John Wiley & Sons. Unless otherwise noted, technical terms are used according to conventional usage. Definitions of common terms in molecular biology maybe found in e.g., Benjamin Lewin, *Genes IX*, published by Oxford University Press, 2007 (ISBN 0763740632); Krebs, et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The term "plant" includes whole plants, plant organs, progeny of whole plants or plant organs, embryos, somatic embryos, embryo-like structures, protocorms, protocorm-like bodies (PLBs), and suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like). The class of plants that can be used in the method of the invention is generally as broad as the class of higher and lower plants amenable to the molecular biology and plant breeding techniques described herein, specifically angiosperms (monocotyledonous (monocots) and dicotyledonous (dicots) plants). It includes plants of a variety of ploidy levels, including aneuploid, polyploid, diploid, haploid and hemizygous. The genetically altered plants described herein alfalfa.

The terms "approximately" and "about" refer to a quantity, level, value or amount that varies by as much as 30%, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria. All references mentioned herein are incorporated by reference.

Having now generally described this invention, the same will be better understood by reference to certain specific examples and the accompanying drawings, which are included herein only to further illustrate the invention and are not intended to limit the scope of the invention as defined by the claims. The examples and drawings describe at least one, but not all embodiments, of the inventions claimed. Indeed, these inventions may be embodied in many different forms and should not be construed as limited to the embodiments set forth herein; rather, these embodiments are provided so that this disclosure will satisfy applicable legal requirements.

Example 1. Hydroxycinnamoyl-CoA:L-DOPA Hydroxycinnamoyl Transferase Activity in Red Clover Tissues For experiments described in this and other examples herein with red clover (*Trifolium pratense*), a highly regenerable genotype (designated NRC7) derived from a population of NewRC germplasm (Smith and Quesenberry, 1995, *Crop Sci.* 35:295-295) was used. For genetically altered alfalfa (*Medicago sativa*), a highly regenerable clone of Regen-SY germplasm (Bingham, 1991, *Crop Sci.* 31:1098) was used for all examples. A collection of NRC7 red clover plants silenced for red clover hydroxycinnamoyl-CoA: malate hydroxycinnamoyl transferase (HMT, encoded by red clover HCT2) was generated as described by Sullivan and Zarnowski, 2011, using the RNAi construct described therein which contains a hairpin RNA corresponding to the region between nucleotides 481 and 1224 of GenBank sequence EU861219.

Further, for all experiments described herein, trans-p-coumaroyl-, -caffeoyl-, and -feruloyl-CoA thioesters were prepared using recombinant *A. thaliana* 4CL1 protein (Lee, et al., 1995 *Plant Mol. Biol.* 28:871-884) produced in *Escherichia coli* using the pET30 expression vector (Novagen, Madison, Wis.) and quantified as detailed in Sullivan, 2009).

To assess the accumulation of hydroxycinnamoyl compounds in plants, tissue samples were ground in liquid nitrogen in a mortar and pestle, or for small samples in a 2 mL screw cap tube with two 4 mm glass beads using a Mini-BeadBeater (Biospec Products, Bartlesville, Okla.). The ground frozen tissue was extracted at room temperature with 10 mL/g 100 mM HCl, 50 mM ascorbic acid. Extracts were filtered through Miracloth (Calbiochem, Billerica, Mass.) or glass wool then centrifuged at 20,000×g at room temperature. 1 mL of the resulting supernatant was applied to a 1 mL ENVI-18 solid phase extraction column (Supelco, St. Louis, Mo., USA) pre-equilibrated with 3×1 mL of methanol and 3×1 mL 0.1% acetic acid in water (pH adjusted to 2.5 with HCl). The column was washed with 3×1 mL 0.1% acetic acid in water (pH adjusted to 2.5 with HCl) and eluted with 1 mL methanol.

The eluate is analyzed for hydroxycinnamates and other phenolics by HPLC. The eluents were analyzed on a Shim-Pack XR-ODS II (C-18) 120 Å column (Shimadzu Scientific Instruments North America, Columbia, Md., USA; 100×2.0 mm×2.2 micron) using a two solvent system [Solvent A: deionized water with 0.1% (v/v) formic acid, Solvent B: acetonitrile] at a flow rate of 0.5 mL/min. The HPLC conditions were 5 min isocratic 2% Solvent B, 10 min gradient to 30% Solvent B, 3 min gradient to 100% Solvent B, 5 min isocratic 100% Solvent B, 0.5 min gradient to 2% Solvent B and 3.5 min isocratic re-equilibration at 2% Solvent B. Compound elution was monitored (250 to 500 nm) with a UV/visible photodiode array detector (PDA). When peaks were quantified, purchased clovamide or free hydroxycinnamic acids were used as standards (Nielsen, et al., 1984, *Phytochem* 23:1741-1743; Sullivan and Zeller, 2012). In some cases, elution was also monitored by mass spectrometry using a MS2020 mass spectrometer (MS) (Shimadzu Scientific Instruments North America) using a dual ion source (electrospray and atmospheric pressure chemical ionization) with data collection in both positive and negative ion modes. MS data was collected between 2.0 and 16.0 min of the HPLC run, scanning for m/z between 50 and 500 u at 7500 u/sec, with detector voltage of 1.3 kV, nebulizing gas flow of 1.5 L/min, drying gas flow of 10 L/min, desolvation line and heat block temperatures of 250° C.

Plant tissue extracts were prepared to assess hydroxycinnamoyl-CoA hydroxycinnamoyl transferase activity. Tissue was powdered in liquid nitrogen using a mortar and pestle or for small samples in a 2 mL screw cap tube with two 4 mm glass beads using a Mini-BeadBeater (Biospec Products, Bartlesville, Okla.). The frozen powdered tissue was added to 1 to 2 mL/g extraction buffer containing 100 mM Na phosphate (pH 7.5), 100 mM ascorbic acid (pH adjusted to 7.5 with NaOH), and 1% (v/v) protease inhibitor cocktail (P-9599, Sigma, St. Louis, Mo.). The frozen, powdered tissue and buffer were thoroughly mixed by stirring or vortex mixing (depending on amount of tissue and volume) until the mixture thawed and reached a temperature of 6 to 8° C. The slurry was filtered through a layer of Miracloth (Calbiochem, Billerica, Mass.) on top of a double layer of cheesecloth, as much liquid as possible was squeezed out, and the filtrate collected on ice. The filtrate was divided among microcentrifuge tubes and centrifuged at 17,000×g at 4° C. for 5 min. The supernatant was removed to fresh microcentrifuge tubes, the centrifugation repeated, and the supernatant retained. Supernatants (typically 30% of the packed column volume) were applied to previously prepared spin columns (1-10 mL syringes packed with Sephadex G-25 Superfine [GE Healthcare, Uppsala, Sweden] equilibrated with 100 mM Na phosphate [pH 7.5 or as specified for individual experiments], and centrifuged for 1 min at 200×g prior to sample application) to remove low molecular weight compounds, and in some cases, to change the pH of the extract. Following supernatant application, the columns were centrifuged for 2 min at 200×g and the flow through (desalted protein extract) retained. Following addition of fresh protease inhibitor cocktail (to 0.5% [v/v]), extracts were divided into 150 to 200 µL aliquots, flash frozen in liquid nitrogen, and stored at −80° C. until needed. In the case of pH adjustment by the spin column procedure, pH was confirmed by spotting a small amount of extract on pH indicator paper. Protein content of the extracts was determined using Bio-Rad Protein Assay (Bio-Rad Laboratories, Hercules, Calif.) using bovine serum albumin as the standard.

In-vitro reactions for hydroxycinnamoyl-CoA transferase activity contained 100 mM sodium phosphate buffer (pH 7.5), 25 to 50 mM ascorbate, 1 to 2 mM p-coumaroyl-, caffeoyl-, or feruloyl-CoA donor substrate, 1 to 6 mM acceptor substrate (L-DOPA, tyrosine, shikimic, or malic acid), and enzyme source (e.g. leaf extracts as prepared above or soluble *E. coli* extract as described below). Reactions were incubated at 30° C. for up to 3 hours then stopped by the addition of ⅕ volume of 10% formic acid. Precipitated protein was removed by centrifugation (17,000×g for 5 min at room temperature). The supernatant is analyzed for reaction products by HPLC with PDA and sometimes MS detection as described above.

Using this approach, a previously undescribed hydroxycinnamoyl-CoA:L-DOPA hydroxycinnamoyl transferase activity (HDT) was detected in unexpanded red clover leaves (15 pkat/mg protein for caffeoyl-CoA donor and L-DOPA acceptor substrates), although no HDT activity could be detected in mature red clover leaves. Among plants transformed with a hairpin RNA RNAi gene silencing construct for HCT2 (which encodes HMT), three independent transformants whose average level of phaselic acid was reduced greater than 100-fold relative to wild type controls also showed greater than 10-fold reductions in clovamide levels relative to wild type controls. In these plants, HMT activity (the target of the silencing transgene) in unexpanded leaves was reduced to undetectable levels, and HDT activity was reduced by nearly 20-fold. Previous experiments with HCT2 gene product produced in *E. coli* indicated that it does not have HDT activity, however (Sullivan, 2009). Based on these results and the data previously published, it was hypothesized that the gene encoding HDT is expressed in unexpanded leaves but not mature leaves. As such, a PCR approach to isolation and identification of a cDNA corresponding to the red clover gene encoding HDT activity was taken.

Example 2. Cloning of Two cDNAs Encoding Hydroxycinnamoyl-CoA:L-DOPA Hydroxycinnamoyl Transferase (HDT1 and HDT2)

Red clover total RNA was prepared from plant tissues using the RNeasy Plant Mini Kit (Qiagen, Valencia, Calif.) according to the manufacturer's recommended protocol. Oligo dT-primed cDNA was prepared using Superscript III reverse transcriptase (Invitrogen, Carlsbad, Calif.) according to the manufacturer's recommended protocol from DNase I-treated total RNA. Plasmid DNA was prepared using the QIAprep Spin Miniprep Kit (Qiagen, Valencia, Calif.) according to the manufacturer's recommended protocol. DNA sequence was determined by Sanger cycle sequencing via reactions using Big Dye v3.1 (Applied Biosystems, Foster City, Calif.). Sequencing reactions were analyzed on ABI 3730xl DNA Analyzers by the University of Wisconsin Biotechnology Center (Madison, Wis.). Sequence analyses were carried out using the Lasergene Version 8 or higher (DNAStar, Madison, Wis.), and BLAST® programs using the National Center for Biotechnology Information (NCBI, ncbi.nlm.nih.gov) web site.

A nested PCR strategy using degenerate primers based on conserved regions of previously cloned red clover hydroxycinnamoyl-CoA:malate and hydroxycinnamoyl-CoA:shikimate hydroxycinnamoyl transferases (GenBank accessions EU861219 and EU861218, respectively) as well as two uncharacterized *Phaseolus vulgaris* putative hydroxycinnamoyl-CoA hydroxycinnamoyl transferases (GenBank Accessions XM_007146186 and XM_007146336) was used to obtain a DNA fragment corresponding to HDT. The PCR was carried out using Phusion® DNA polymerase (New England Biolabs, Ipswich, Mass.). The first round PCR reaction (50 µL) contained 1 X Phusion® HF Buffer, 200 µM dNTP, cDNA equivalent to 100 ng total RNA from unexpanded red clover leaves (prepared as described above), 1 unit Phusion® DNA polymerase, 1 µM each primers ms809 (SEQ ID NO: 5) and ms815 (SEQ ID NO: 6) (Table 3, infra). The PCR reaction was incubated for 30 sec at 98° C. in the preheated block of a thermocycler. This incubation was followed by 35 cycles of 98° C. for 10 sec (denaturation), 55° C. for 20 sec (annealing), and 72° C. for 30 sec (extension) followed by a final 5 min extension at 72° C. 20 µL of the PCR reaction was resolved via electrophoresis on a 1.0% agarose gel using standard techniques (Sambrook, et al., 2012). An approximately 1000 bp DNA fragment was excised from the gel and purified using QiaEx® resin (silica-gel particles) (Qiagen Inc., Germantown, Md.) according to the manufacturer's recommended procedure.

A second round (nested) PCR reaction (25 µL) contained 1X Phusion® HF Buffer, 200 µM dNTP, gel purified first round PCR product equivalent to 0.01 µL of the first round reaction, 0.5 units Phusion® DNA polymerase, 0.5 µM each primers ms867 (SEQ ID NO: 7) and ms870 (SEQ ID NO: 8) (Table 3, infra). The PCR reaction was incubated for 30 sec at 98° C. in the preheated block of a thermocycler. This incubation was followed by 35 cycles of 98° C. for 10 sec (denaturation), 49° C. for 20 sec (annealing), and 72° C. for 30 sec (extension) followed by a final 5 min extension at 72° C. 20 µL of the PCR reaction was resolved via electrophoresis on a 1.0% agarose gel using standard techniques. An approximately 700 bp DNA fragment was excised from the gel and purified using QiaEx® resin (silica-gel particles) (Qiagen Inc., Germantown, Md.) according to the manufacturer's recommended procedure. The DNA fragment was cloned into pGEM T-Easy (Promega Corp., Madison, Wis.) according to the manufacturer's recommended protocol.

Sequence of the resulting DNA fragment was used to design primers for 5' and 3' RACE (rapid amplification of cDNA ends). 5' and 3' RACE were carried out using the SMARTer® RACE cDNA Amplification Kit (Catalog #634923, Clontech Laboratories, Mountain View, Calif.) using total RNA from unexpanded red clover leaves and ms881 (SEQ ID NO: 9) and ms882 (SEQ ID NO: 10) (see Table 3, infra) as the gene specific primers for 5' and 3' RACE, respectively. The resulting 5' and 3' RACE products were gel purified as described above and cloned into pGEM T-Easy (Promega Corp., Madison, Wis.) as described above. Sequencing of the resulting fragments was used to design primers ms884 (SEQ ID NO: 11) and ms885 (SEQ ID NO: 12) (see Table 3, infra) for end to end PCR. Three independent end to end PCR reactions (25 µL each) contained 1X Phusion® HF Buffer, 200 µM dNTP, first strand 5' RACE cDNA (equivalent to 17 ng total RNA), 0.5 units Phusion® DNA polymerase, 0.5 µM each primers ms884 (SEQ ID NO: 11) and ms885 (SEQ ID NO: 12). The resulting DNA fragments were cloned into pGEM T-Easy (Promega Corp., Madison, Wis.) according to the manufacturer's recommended protocol and several clones from each PCR reactions were sequenced.

Degenerate oligonucleotide PCR primers were designed based on several conserved regions of red clover HCT2, red clover HCT1 (encoding hydroxycinnamoyl-CoA:shikimate hydroxycinnamoyl transferase, Genbank EU861218), and two other uncharacterized putative hydroxycinnamoyl transferase genes (Genbank XM_007146186 and XM_007146336) from *Phaseolus vulgaris*, another legume species. These primers were used in nested PCR reactions to generate an approximately 700 bp DNA fragment. Sequence analysis of the fragment revealed that it was distinct from the red clover HCT2 sequence (80% identity) and allowed primers to be designed for 5' and 3' RACE (rapid amplification of mRNA ends) as described above. The resulting RACE products were sequenced and used to design primers for end-to-end PCR to generate full-length clones corresponding to the putative HDT cDNA. For end-to-end PCR, a high fidelity proofreading thermostable DNA polymerase was used, and clones were isolated and sequenced from three independent PCR reactions allowing authentic alleles of the putative HDT gene to be distinguished from PCR errors (true alleles or closely related members of a multigene family would be expected to be represented in all three independent PCR reactions, whereas this would be unlikely for nucleotide changes resulting from DNA polymerase misincorporation).

Using this approach, two distinct 1451 bp cDNAs (SEQ ID NO: 1 (HDT1) and SEQ ID NO: 3 (HDT2), respectively) were identified. The cDNAs are >99% identical and are predicted to encode 452 amino acid proteins (SEQ ID NO: 2 (HDT1) and SEQ ID NO: 4 (HDT2), respectively) that are >98% identical. For red clover sequences in GenBank, the following high similarity (>90% identity over >50 bp) matches to HDT1 were found: emb|LN846355.1, unannotated genome assembly (97% identity over 847 nt, from 15778318 to 15777475, 95% identity over 400 nt from 15779814 to 15779415); gb|ASHM01031115.1, unannotated whole genome shotgun sequence (99% identity over 530 bp from nt 2103 to 1574, 99% identity from 484 to 1); gb|ASHM01105919.1, unannotated whole genome shotgun sequence (99% identity over 484 nt from 484 to 1); emb|CVOM01002144.1, unannotated whole genome shotgut sequence (99% identity over 455 nt from 6373 to 6827, 99% identity over 251 nt from 7003 to 7253, 99% identity over 245 bp from 5443 to 5687, 94% identity over 79 bases from 6273 to 6351); gb|ASHM01081496.1, unannotated whole genome shotgun sequence (99% identity over 360 bp from 1011 to 652); emb|CVOM01021691.1, unannotated whole genome shotgun sequence (99% identity over 223 bp, from 1 to 223); gb|ASHM01023500.1, unanotated whole genome shotgun sequence (94% identity over 62 bases from 423 to 362); emb|CVOM01010076.1, unannotated whole genome shotgun sequence (100% identity over 62 bp from 62 to 1); ebm|CVOM01001690.1, 94% identity over 62 bases from 1270 to 1331); gb|GAOU01004675.1, unannotated shotgun transcriptome assembly (99% identity over 697 nt from 299 to 995); gb|GAOU01036897.1, unannotated shotgun transcriptome assembly (100% identity over 358 bp from 358 to 1); gb|GAOU01021755.1, unannotated shotgun transcriptome assembly (100% identity over 304 bp from 5 to 308); gb|GAOU01027645.1, unannotated shotgun transcriptome assembly (100% identity over 102 bp from 831 to 730).

The best nucleotide sequence matches (83% sequence identity with 100% coverage) from species other than red clover are XM_003598989.2 and CU468290.9 from *Medicago truncatula*. XM_003598989.2 is annotated as "spermidine hydroxycinnamoyl transferase" based on EVidenceModeler gene annotation software. Proteins of these encoded genes are 75% identical to the proteins (SEQ ID NO: 2 and SEQ ID NO: 4, respectively) encoded by the cloned red clover HDT cDNAs (SEQ ID NO: 1 and SEQ ID NO: 3, respectively). Other top matches are similarly annotated as spermidine hydroxycinnamoyl transferase, or hydroxycinnamoyl transferase-like. Most or all annotations do not appear to be based on experimental biochemical data, however.

Example 3. Evaluation of HDT mRNA Levels in Red Clover Leaves by Reverse Transcription PCR Expression of HDT was evaluated using semiquantitative reverse transcribed PCR using cDNA from unexpanded or mature red clover leaves as the template. PCR reactions contained 25 pmol each ms881 (SEQ ID NO: 9) and ms882 (SEQ ID NO: 10) (for detection of HDT) or ms171 (SEQ ID NO: 17) and ms172 (SEQ ID NO: 18) (for detection of actin, as a control) (see Table 3), cDNA equivalent to 50 ng total RNA, 12.5 µL EconoTaq Plus Green Mastermix (Lucigen Corp., Middleton, Wis.) and water to make 25 µL. Reactions were incubated for 30 sec at 94° C. in the block of a thermocycler. This incubation was followed by 25 cycles of 94° C. for 20 sec (denaturation), 64° C. for 20 sec (annealing), and 72° C. for 30 sec (extension) followed by a final 2 min extension at 72° C. 3 µL of the PCR reactions were resolved via electrophoresis on a 1.5% agarose gel using standard techniques.

HDT expression was much higher in unexpanded leaves than in mature leaves. Expression of a control gene, actin, was similar between unexpanded and mature leaves. Based on these data, expression of the cloned HDT gene (higher in unexpanded leaves) is consistent with the relative HDT enzyme activity measured in these tissues.

TABLE 3

| Designation | Sequence (5' to 3') |
|---|---|
| ms809 | TWYTAYCCWDTRGCTGGHMG (SEQ ID NO: 5) |
| ms815 | AYWGSCYTYCCMYAWCCAAAATC (SEQ ID NO: 6) |
| ms867 | AMTTCATCAAYWCATGGKC (SEQ ID NO: 7) |
| ms870 | CCAAAATCWGMWTCRTRAAHVGG (SEQ ID NO: 8) |
| ms881 | CTGGATACCTAGAACATCTTCTTCATTGGC (SEQ ID NO: 9) |
| ms882 | CACCTTTGGAGCCACGTTTTGAACACTTGG (SEQ ID NO: 10) |
| ms884 | CAACACAGAACTTCAASCTAGCATACC (SEQ ID NO: 11) |
| ms885 | ACCAACTTAGAGGGTGATTTTGGGTC (SEQ ID NO: 12) |
| ms886 | CGGGCCATGGTAACCATTATAGCTTCTCAC (SEQ ID NO: 13) |
| ms887 | GGGCCTCGAGTCATATCTCCTCATAAAAATACTTGTT (SEQ ID NO: 14) |
| ms888 | GTCTAGAAAACAATGGTAACCATTATAGCTTCTCAC (SEQ ID NO: 15) |

TABLE 3-continued

| Designation | Sequence (5' to 3') |
|---|---|
| ms889 | CGGTACCTCATATCTCCTCATAAAAATACTTGTT (SEQ ID NO: 16) |
| ms170 | GGTGTGAGTCACACTGTGCCAATCT (SEQ ID NO: 17) |
| ms171 | CGGAACCTCTCAGCTCCAATTGTGA (SEQ ID NO: 18) |

Example 4. Enzymatic Activity of HDT1 and HDT2 Produced in *E. coli*

To determine whether the cloned red clover cDNAs (HDT1 and HDT2) possess hydroxycinnamoyl-CoA:L-DOPA hydroxycinnamoyl transferase activity, the open reading frames were placed behind the IPTG-inducible promoter of the pET28 expression vector and expressed in *E. coli*. Plasmids containing full-length red clover HDT coding regions (both HDT1 (SEQ ID NO: 1) and HDT2 (SEQ ID NO: 3)) were used as templates in PCR reactions with primers designed to introduce an NdeI restriction site at the start codons (ms886—SEQ ID NO: 13) and an XhoI site immediately following the stop codon (ms887—SEQ ID NO: 14) of each open reading frame. The resulting PCR products were digested with NcoI and XhoI and inserted into pET28a (Novagen, Madison, Wis.) digested with NcoI and XhoI. The insert is operably linked to the IPTG-inducible promoter contained in pET28. Each plasmid was sequenced to confirm correct sequence was generated.

Each pET28 derivative containing HDT coding regions (pET28-HDT1 and pET28-HDT2) or pET28 (as a negative control) were transformed, individually, into BL21(DE3) RIL Codon Plus *E. coli* (Agilent Technologies, Santa Clara, Calif.). Cultures of *E. coli* harboring HDT-containing plasmids (BL21/pET28-HDT1; BL21/pET28-HDT2) or control empty vector plasmid (BL21/pET28) were grown at 37° C. with shaking (225 rpm) in TB medium (per L: 12 g tryptone, 24 g yeast extract, 4 mL glycerol, 2.3 g $KH_2PO_4$, 12.5 $K_2HPO_4$) supplemented with 50 µg/mL kanamycin and 34 µg/mL chloramphenical to an $OD_{600\ nm}$ of approximately 1.5. Cultures were cooled on ice to approximately 10° C., induced by addition of isopropyl-beta-D-thiogalactopyranoside (IPTG) to 1 mM, and incubated at 10° C. with shaking (150 rpm) for an additional 20 hours. Cultures were lysed using BugBuster reagent (Novagen) according to the manufacturer's suggested procedures and fractionated into soluble and insoluble portions. The soluble fraction was isolated, divided into single use aliquots, flash frozen in liquid nitrogen and stored at −80° C. until ready to use.

To assess if either HDT1 or HDT2 proteins possessed the anticipated enzymatic activity, in-vitro reactions for hydroxycinnamoyl-CoA transferase activity contained 100 mM sodium phosphate buffer (pH 7.5), 25 mM ascorbate, 1 mM p-coumaroyl-, caffeoyl-, or feruloyl-CoA donor substrate, 1 mM acceptor substrate (L-DOPA or L-tyrosine), and soluble *E. coli* extract (BL21/pET28-HDT1; BL21/pET28-HDT2; or BL21/pET28). Reactions were incubated at 30° C. for up 1 hour then stopped by the addition of ⅕ volume of 10% formic acid. Precipitated protein was removed by centrifugation (17,000×g for 5 min at room temperature).

Figure 4B:
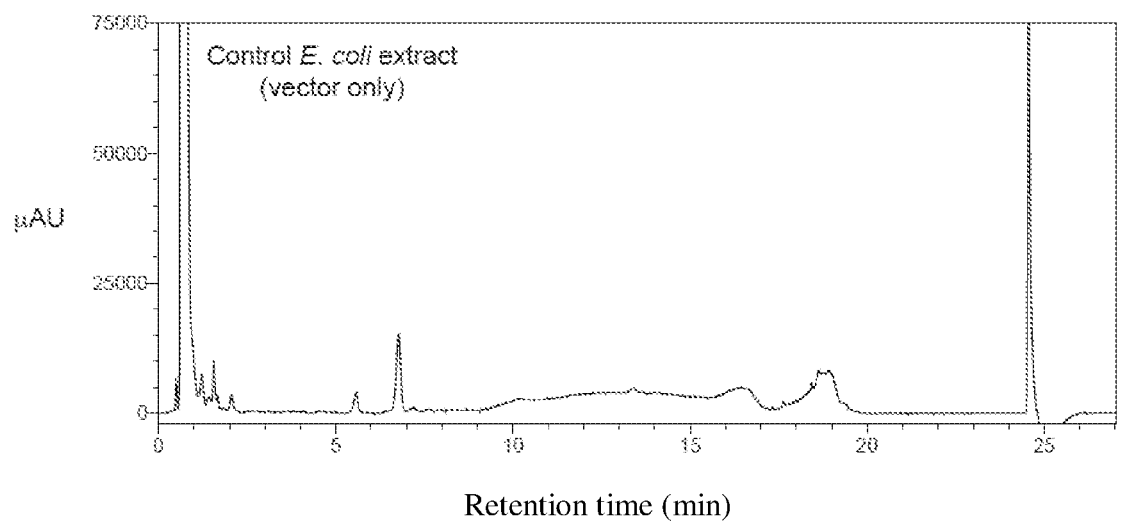
FIG. 4B is the reverse phase HPLC of the in-vitro reaction of E. coli BL21/pET28 (negative control) extract with caffeoyl-CoA donor substrate and L-DOPA substrate, producing no clovamide peak.
Figure 4C:
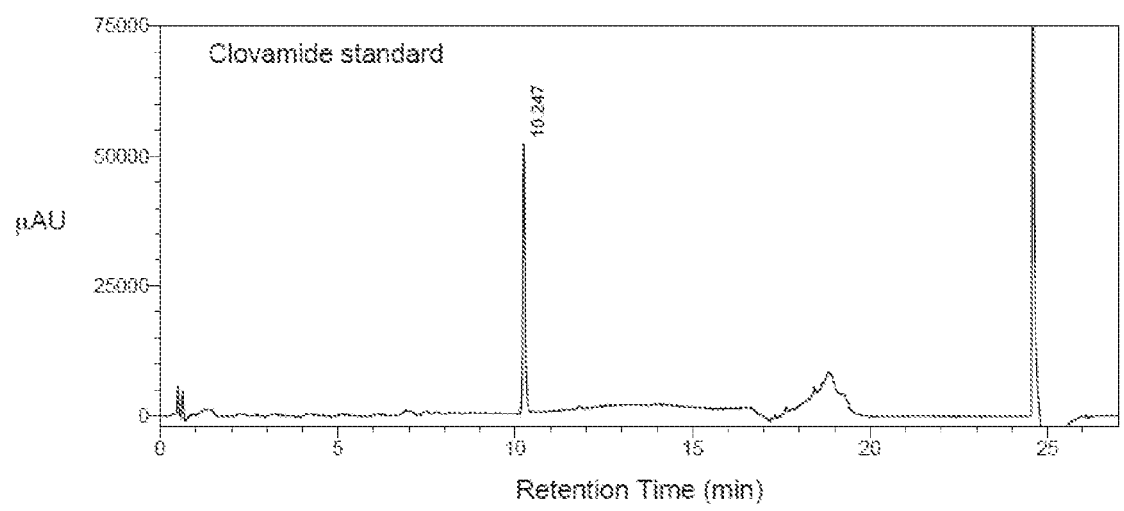
FIG. 4C is the reverse phase HPLC of a clovamide standard demonstrating its retention time at approximately 10.247 minutes.

The supernatant is analyzed for reaction products by HPLC. Phenolic samples from the in-vitro reactions were analyzed on a Shim-Pack XR-ODS II (C-18) 120 Å column (Shimadzu Scientific Instruments North America, Columbia, Md., USA; 100×2.0 mm×2.2 micron) using a two solvent system [Solvent A: deionized water with 0.1% (v/v) formic acid, Solvent B: acetonitrile] at a flow rate of 0.5 mL/min. The HPLC conditions were 5 min isocratic 2% Solvent B, 10 min gradient to 30% Solvent B, 3 min gradient to 100% Solvent B, 5 min isocratic 100% Solvent B, 0.5 min gradient to 2% Solvent B and 3.5 min isocratic re-equilibration at 2% Solvent B. Compound elution was monitored (250 to 500 nm) with a UV/visible photodiode array detector (PDA). FIG. 4A shows the reverse phase HPLC of the in-vitro reaction of *E. coli* BL21/pET28-HDT1 extract with caffeoyl-CoA and L-DOPA showing clovamide peak at approximately 10.245; FIG. 4B shows the reverse phase HPLC of the in-vitro reaction of *E. coli* BL21/pET28 (negative control) with caffeoyl-CoA and L-DOPA showing no clovamide peak; and FIG. 4C shows reverse phase HPCL of pure clovamide with peak at approximately 10.245. Data for *E. coli* BL21/pET28-HDT2 is not shown but is similar to the data of BL21/pET-HDT1 (FIG. 4A).

In-vitro reactions of extracts of BL21/pET28-HDT1 or BL21/pET28-HDT2 with caffeoyl-CoA and L-tyrosine or with p-coumaroyl- or feruloyl-CoA donors and L-DOPA or L-tyrosine acceptors also produced the expected products. In-vitro reactions with any of the hydroxycinnamoyl-CoA donors and L-DOPA or L-tyrosine acceptors with BL21/pET28 (negative control) extract failed to produce any hydroxycinnamoyl-amide products.

When expressed in *E. coli*, the protein products of the cloned HDT cDNAs (both HDT1 and HDT2) are capable of transferring a trans-hydroxycinnamoyl moiety from the corresponding CoA derivative (p-coumaroyl-, caffeoyl-, and feruloyl-CoA) to L-DOPA or L-tyrosine using similar in-vitro assays as described above. See FIG. 3.

Example 5. Genetically Altered Alfalfa Expressing Red Clover HDT1 or HDT2

For expression of either HDT1 or HDT2 in genetically altered alfalfa, PCR primer pairs were designed to introduce XbaI (ms888—SEQ ID NO: 15) and KpnI (ms889—SEQ ID NO: 16) restriction endonuclease sites flanking the 5' and 3' ends of the coding regions of the two red clover HDT genes (HDT1 and HDT2). Additionally, the forward primer provided the proposed dicot consensus sequence AAACA (Joshi, et al., 1997, *Plant Mol. Biol.* 35:993-1001) immediately upstream of the initiating methionine codon. This primer pair was used in PCR reactions with plasmids containing the full-length red clover HDT1 or HDT2 coding regions as templates. The resulting PCR fragments were cloned as XbaI-KpnI fragments downstream of the CsVMV promoter (Verdaguer, et al., 1996, *Plant Mol. Biol.* 31:1129-1139) in a derivative of pBIB-HYG plant transformation vector (Becker, 1990, *Nucleic Acids Res.* 18:203-203; Verdonk and Sullivan, 2013, *Botany* 91:117-122). The cloned inserts were sequenced to confirm that no mutations occurred.

HDT plant expression constructs containing a selectable marker for hygromycin resistance (pBIB-HYG/HDT1; pBIB-HYG/HDT2) or empty vector containing selectable marker for hygromycin resistance (pBIB-HYG—negative control) were transformed into *Agrobacterium tumefaciens* strain LBA4404 (Hellens, et al., 2000, *Trends Plant Sci.* 5:446-451). The resulting *A. tumefaciens* strains were used to genetically modify a highly regenerable clone of Regen-SY alfalfa (Bingham, 1991) as previously described (Samac and Austin-Phillips, 2006, *Alfalfa* (*Medicago sativa* L.), in Wang, ed., Agrobacterium Protocols, 2nd Edition. Humana Press, Totowa, N.J., pp 301-311). Briefly, 12-15 leaves of alfalfa are cut into 6 pieces each. The leaf pieces are dipped in a suspension of *Agrobacterium* containing pBIB-HYG/HDT1, pBIB-HYG/HDT2, or pBIB-HYG. The leaf pieces are co-cultivated with the *Agrobacterium* for one week on non-selective medium. Following co-cultivation, the leaf pieces are transferred to hygromycin containing medium to allow selection of transformed cells. Whole plants are regenerated from transformed cells via somatic embryogenesis using a series of media with differing hormone compositions. The resulting genetically altered alfalfa have the T-DNA region of pBIB-HYG/HDT1, pBIB-HYG/HDT2, or pBIB-HYG integrated into their genomes. The genetically altered alfalfa were allowed to grow and leaves were harvested.

To assess the accumulation of hydroxycinnamoyl compounds, tissue samples of each genetically altered alfalfa plant were ground in liquid nitrogen in a mortar and pestle, or for small samples in a 2 mL screw cap tube with two 4 mm glass beads using a Mini-BeadBeater (Biospec Products, Bartlesville, Okla.). The ground frozen tissue was extracted at room temperature with 10 mL/g 100 mM HCl, 50 mM ascorbic acid. Extracts were filtered through Miracloth (Calbiochem, Billerica, Mass.) or glass wool then centrifuged at 20,000×g at room temperature. 1 mL of the resulting supernatant was applied to a 1 mL ENVI-18 solid phase extraction column (Supelco, St. Louis, Mo., USA) pre-equilibrated with 3×1 mL of methanol and 3×1 mL 0.1% acetic acid in water (pH adjusted to 2.5 with HCl). The column was washed with 3×1 mL 0.1% acetic acid in water (pH adjusted to 2.5 with HCl) and eluted with 1 mL methanol.

Tissue was powdered in liquid nitrogen using a mortar and pestle or for small samples in a 2 mL screw cap tube with two 4 mm glass beads using a Mini-BeadBeater (Biospec Products, Bartlesville, Okla.). The frozen powdered tissue was added to 1 to 2 mL/g extraction buffer containing 100 mM Na phosphate (pH 7.5), 100 mM ascorbic acid (pH adjusted to 7.5 with NaOH), and 1% (v/v) protease inhibitor cocktail (P-9599, Sigma, St. Louis, Mo.). The frozen, powdered tissue and buffer were thoroughly mixed by stirring or vortex mixing (depending on amount of tissue and volume) until the mixture thawed and reached a temperature of 6 to 8° C. The slurry was filtered through a layer of Miracloth (Calbiochem, Billerica, Mass.) on top of a double layer of cheesecloth, as much liquid as possible was squeezed out, and the filtrate collected on ice. The filtrate was divided among microcentrifuge tubes and centrifuged at 17,000×g at 4° C. for 5 min. The supernatant was removed to fresh microcentrifuge tubes, the centrifugation repeated, and the supernatant retained. Supernatants (typically 30% of the packed column volume) were applied to previously prepared spin columns (1-10 mL syringes packed with Sephadex G-25 Superfine [GE Healthcare, Uppsala, Sweden] equilibrated with 100 mM Na phosphate [pH 7.5 or as specified for individual experiments], and centrifuged for 1 min at 200×g prior to sample application) to remove low molecular weight compounds, and in some cases, to change the pH of the extract. Following supernatant application, the columns were centrifuged for 2 min at 200×g and the flow through (desalted protein extract) retained. Following addition of fresh protease inhibitor cocktail (to 0.5% [v/v]), extracts were divided into 150 to 200 µL aliquots, flash frozen in liquid nitrogen, and stored at −80° C. until needed. In the case of pH adjustment by the spin column procedure, pH was confirmed by spotting a small amount of extract on pH indicator paper. Protein content of the extracts was determined using Bio-Rad Protein Assay (Bio-Rad Laboratories, Hercules, Calif.) using bovine serum albumin as the standard.

Phenolics from the leaves of the genetically altered alfalfa plants containing pBIB-HYG/HDT1, pBIB-HYG/HDT2, or pBIB-HYG were extracted and analyzed by HPLC with PDA and MS detection. The HPLC protocol used is provided above. For MS detection, elution was also monitored with a MS2020 mass spectrometer (MS) (Shimadzu Scientific Instruments North America) using a dual ion source (electrospray and atmospheric pressure chemical ionization) with data collection in both positive and negative ion modes. MS data was collected between 2.0 and 16.0 min of the HPLC run, scanning for m/z between 50 and 500 u at 7500 u/sec, with detector voltage of 1.3 kV, nebulizing gas flow of 1.5 L/min, drying gas flow of 10 L/min, desolvation line and heat block temperatures of 250° C. When peaks were quantified, purchased clovamide or free hydroxycinnamic acids were used as standards (Nielsen, et al., 1984, *Phytochem* 23:1741-1743; Sullivan and Zeller, 2012).

Compared to genetically altered plants with only the vector (pBIB-HYG), several of the genetically altered plants containing either pBIB-HYG/HDT1 or pBIB-HYG/HDT2 showed the presence of new phenolics. Two of the detected peaks have m/z=−326 by MS, the expected negative ion of the amide that would be formed between p-coumaric acid and L-tyrosine. One of these is indistinguishable from trans-p-coumaroyl-L-tyrosine formed in-vitro using *E. coli* BL21/pET28-HDT1 in terms of retention time, UV absorption spectrum, and m/z. The second m/z=−326 peak is likely the cis isomer, since cis isomers of hydroxycinnamic acid derivatives, especially p-coumaroyl and feruloyl) are known to form in planta (Sullivan, 2014, Planta 239:1091-1100). Two other of the detected peaks have m/z=−356 by MS, the expected negative ion of the amide that would be formed between ferulic acid and tyrosine. One of these is indistinguishable from trans-feruloyl-L-tyrosine formed in-vitro using *E. coli* BL21/pET28-HDT1 or BL21/pET28-HDT2 in terms of retention time, UV absorption spectrum, and m/z. The second m/z=−356 peak is likely the cis isomer as described above for p-coumaroyl-L-tyrosine. Additionally, when protein extracts were made from of two independent genetically altered alfalfa plants expressing the red clover either HDT1 or HDT2 gene, they had enzymatic activity capable of transferring caffeic acid moieties from caffeoyl-CoA to L-tryosine or L-DOPA. No enzymatic activity capable of transferring caffeoyl-CoA to L-tyrosine or L-DOPA was detected in the leaves of a control alfalfa plant transformed with the empty pBIB-HYG vector. These results indicate that active hydroxycinnamoyl-CoA:L-DOPA/tyrosine hydroxycinnamoyl transferase is present in alfalfa when the red clover either HDT1 or HDT2 transgenes are present.

Genetically altered alfalfa containing pBIB-HYG/HDT1 or pBIB-HYG/HDT2 are allowed to grow for several months until harvesting. The genetically altered alfalfa are assayed for the present of clovamide and related hydroxycinnamoyl amides using LC-MS protocols described above. The genetically altered alfalfa contain clovadime, N-caffeoyl-L-tyrosine, N-p-coumaroyl-L-DOPA, and N-feruloyl-L-DOPA. The genetically altered alfalfa containing pBIB-HYG/HDT1 or pBIB-HYG/HDT2 are also assessed for post-harvest protein degradation in the presence of PPO (also produced by a transgene) using the protocols set forth in U.S. Pat. No. 8,338,339. The genetically altered alfalfa have less post-harvest protein degradation than occurs in wild-type alfalfa. Thus, clovamide and related hydroxycinnamoyl amides produced by HDT1 and/or HDT2 result in the genetically altered alfalfa (a forage crop) having a polyphenol oxidase system (PPO) which provides post-harvest protein protection (from degradation).

Example 6. Utilization of HDT1 or HDT2 Sequence for Rapid Trait Introgression and Accurate Gene Stacking for Clovamide Production Coupled with Marker Assisted Selection Isolation of the HDT1 and HDT2 genes from red clover and the generation of genetically altered alfalfa that contain one of these genes, the genetically altered alfalfa being able to produce hydroxycinnamoyl-CoA:L-DOPA/tyrosine hydroxycinnamoyl transferase and clovamide, has the potential to reduce protein degradation post-harvest in alfalfa. The identification of the cDNA sequences of the HDT1 and HDT2 genes also led to the development of DNA markers which can be used to screen molecularly altered plants rapidly to improve determine plants containing these genes and thus have the phenotype of reduction of post-harvest protein degradation. Genetically altered plants can be achieved by rapid introgression of one of the HDT1 and HDT2 genes. One can use the primers having SEQ ID NO: 9 or SEQ ID NO: 10 to identify these genetically altered plants very early in plant development, at two to three leaf stage, providing great savings in time, space, effort and cost during actual introgression. These primers provide accuracy towards identification of genetically altered plants containing either HDT1 or HDT2 gene. Application of correct gene stacks (for example, when combined with HDT1 or HDT2) and rapid introgression into elite plant lines coupled with marker assay is a valuable application of the discovery of the HDT1 and HDT2 genes that encode hydroxycinnamoyl-CoA:L-DOPA/tyrosine hydroxycinnamoyl transferase and for the ability of the genetically altered plant to produce clovamide which reduces post-harvest protein degradation.

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention. All references cited herein are incorporated by reference.

The invention claimed is:

1. An expression cassette comprising a heterologous promoter operably linked to a cDNA, said cDNA comprising a nucleotide sequence selected from the group consisting of SEQ ID NO: 1, SEQ ID NO: 3, a sequence that is at least 95% identical to SEQ ID NO: 1, and a sequence that is at least 95% identical to SEQ ID NO: 3,
   wherein said cDNA encodes a protein with hydroxycinnamoyl-CoA:L-DOPA/tyrosine hydroxycinnamoyl transferase activity.

2. An expression cassette comprising a heterologous promoter probably linked to a cDNA that encodes a hydroxycinnamoyl-CoA:L-DOPA/tyrosine hydroxycinnamoyl transferase, said cDNA comprising a nucleotide sequence that encodes a hydroxycinnamoyl-CoA:L-DOPA/tyrosine hydroxycinnamoyl transferase,
   wherein said hydroxycinnamoyl-CoA:L-DOPA/tyrosine hydroxycinnamoyl transferase has an amino acid sequence selected from the group consisting of SEQ ID NO: 2, SEQ ID NO: 4, a sequence that is at least 95% identical to SEQ ID NO: 2, and a sequence that is at least 95% identical to SEQ ID NO: 4.

3. A kit for determining if an alfalfa plant contains HDT1 or HDT2 gene and thereby produces a hydroxycinnamoyl-CoA:L-DOPA/tyrosine hydroxycinnamoyl transferase, said kit comprising:
   at least one pair of polynucleotides; and
   an identifying dye,
   wherein said at least one pair of said polynucleotides have the sequence of SEQ ID NO: 9 and SEQ ID NO: 10.

4. The kit of claim 3, further comprising instructions for using said at least one pair of polynucleotides to determine if said alfalfa plant contains said HDT1 or HDT2 gene.

* * * * *

SEQUENCE LISTING

```
<160> NUMBER OF SEQ ID NOS: 18

<210> SEQ ID NO 1
<211> LENGTH: 1451
<212> TYPE: DNA
<213> ORGANISM: Trifolium pratense

<400> SEQUENCE: 1
caacacagaa cttcaagcta gcataccaaa aaaaaaaaat ggtaaccatt atagcttctc      60
acactgtgat tccagaagaa ccaactccac aaggtccatt ttggctctct gatatggatc     120
aagtggttcg tatccgcgac gtaccaactc tttacattta caaacacca aagaaaaacc      180 aagaaaacaa aaacatagta gaaaccttta aaaactctct aagcaaaatt cttgttcact     240
actatcctat agctggtaga ttgtgttaca tagaaggtgg tagattagaa ttgaatctca     300
atgcaaaagg agctattttg gttgaagctg aaacagaaaa aacaatgaat gattatggtg     360
acttttcaca ttttgacacc atcaaagaac ttgttccaat gattgattac aatcaaccaa     420
ttgaagaaat tccaaatttt gttgtgcaac tcacaaattt caaaaacaat gaaggctttg     480
caattggtgt tgctttttctc catcctttat cagatggatt gggagccatt aaattcatca     540
actcatgggc caaaatagca agaggtgaaa cacttgaggc taatgagtta ccatttttgg     600
atagaaaact tctcaaattt tcacacacac ctttggagcc acgttttgaa cacttggagt     660
tgaagccact accactcatt ctaggtagaa aagatgcaag tgaagaaaaa gagaagaaaa     720
cttcagcaac attgttgaaa ctttcatcag aacaagttga taagttgaag aaaaaagcca     780
atgaagaaga tgttctaggt atccagaaaa aagagtactc aaggccttat agtaaatttg     840
aagtaattag tgcacatata tggagatgtg catctaaggc acgtgagctt gaagataatc     900
aagaaagtgt tattagattc attgctgatg ttaaaaatag aatgattcca ccacttccta     960
aaactatttt tgggaatgct ttgactcaaa cagctactaa agggtatatt ggagaaatca    1020
```

-continued

```
catcaaagcc tttgggttac gtggcacaaa agataaggga agcaactgag ttgataaatg    1080
atgagtatat aaggtcacaa attgatgttg ttagaagttt tgaacatttg gatgatgcac    1140
gaaaaatgtt tataggtgaa aaggctcgat attttggtaa tccaaatttt aatttgacta    1200
gttggttaag tatgcctgtt tatgaagctg attttggatg ggggaaacct aattactttg    1260
gattagctga tgtctcacca catgatagag cagtcattct tcttagtcct gatgatgatg    1320
gatctgttct tgtgtctttc cattttcaga ttgcacatat ggagcttttc aacaagtatt    1380
tttatgagga gatatgaaat aggggtggtt ttttgggtcaa ttttgaccc aaaatcaccc     1440 tctaagttgg t                                                         1451
```

<210> SEQ ID NO 2
<211> LENGTH: 452
<212> TYPE: PRT
<213> ORGANISM: Trifolium pratense

<400> SEQUENCE: 2

```
Met Val Thr Ile Ile Ala Ser His Thr Val Ile Pro Glu Glu Pro Thr
1               5                   10                  15

Pro Gln Gly Pro Phe Trp Leu Ser Asp Met Asp Gln Val Val Arg Ile
            20                  25                  30

Arg Asp Val Pro Thr Leu Tyr Ile Tyr Lys Thr Pro Lys Lys Asn Gln
        35                  40                  45

Glu Asn Lys Asn Ile Val Glu Thr Phe Lys Asn Ser Leu Ser Lys Ile
    50                  55                  60

Leu Val His Tyr Tyr Pro Ile Ala Gly Arg Leu Cys Tyr Ile Glu Gly
65                  70                  75                  80

Gly Arg Leu Glu Leu Asn Leu Asn Ala Lys Gly Ala Ile Leu Val Glu
                85                  90                  95

Ala Glu Thr Glu Lys Thr Met Asn Asp Tyr Gly Asp Phe Ser His Phe
            100                 105                 110

Asp Thr Ile Lys Glu Leu Val Pro Met Ile Asp Tyr Asn Gln Pro Ile
        115                 120                 125

Glu Glu Ile Pro Asn Phe Val Val Gln Leu Thr Asn Phe Lys Asn Asn
    130                 135                 140

Glu Gly Phe Ala Ile Gly Val Ala Phe Leu His Pro Leu Ser Asp Gly
145                 150                 155                 160

Leu Gly Ala Ile Lys Phe Ile Asn Ser Trp Ala Lys Ile Ala Arg Gly
                165                 170                 175

Glu Thr Leu Glu Ala Asn Glu Leu Pro Phe Leu Asp Arg Lys Leu Leu
            180                 185                 190

Lys Phe Ser His Thr Pro Leu Glu Pro Arg Phe Glu His Leu Glu Leu
        195                 200                 205

Lys Pro Leu Pro Leu Ile Leu Gly Arg Lys Asp Ala Ser Glu Glu Lys
    210                 215                 220

Glu Lys Lys Thr Ser Ala Thr Leu Leu Lys Leu Ser Ser Glu Gln Val
225                 230                 235                 240

Asp Lys Leu Lys Lys Lys Ala Asn Glu Glu Asp Val Leu Gly Ile Gln
                245                 250                 255

Lys Lys Glu Tyr Ser Arg Pro Tyr Ser Lys Phe Glu Val Ile Ser Ala
            260                 265                 270

His Ile Trp Arg Cys Ala Ser Lys Ala Arg Glu Leu Glu Asp Asn Gln
        275                 280                 285

Glu Ser Val Ile Arg Phe Ile Ala Asp Val Lys Asn Arg Met Ile Pro
```

```
        290                 295                 300
Pro Leu Pro Lys Asn Tyr Phe Gly Asn Ala Leu Thr Gln Thr Ala Thr
305                 310                 315                 320

Lys Gly Tyr Ile Gly Glu Ile Thr Ser Lys Pro Leu Gly Tyr Val Ala
                325                 330                 335

Gln Lys Ile Arg Glu Ala Thr Glu Leu Ile Asn Asp Glu Tyr Ile Arg
            340                 345                 350

Ser Gln Ile Asp Val Val Arg Ser Phe Glu His Leu Asp Asp Ala Arg
        355                 360                 365

Lys Met Phe Ile Gly Glu Lys Ala Arg Tyr Phe Gly Asn Pro Asn Phe
    370                 375                 380

Asn Leu Thr Ser Trp Leu Ser Met Pro Val Tyr Glu Ala Asp Phe Gly
385                 390                 395                 400

Trp Gly Lys Pro Asn Tyr Phe Gly Leu Ala Asp Val Ser Pro His Asp
                405                 410                 415

Arg Ala Val Ile Leu Leu Ser Pro Asp Asp Asp Gly Ser Val Leu Val
            420                 425                 430

Ser Phe His Phe Gln Ile Ala His Met Glu Leu Phe Asn Lys Tyr Phe
        435                 440                 445

Tyr Glu Glu Ile
    450

<210> SEQ ID NO 3
<211> LENGTH: 1451
<212> TYPE: DNA
<213> ORGANISM: Trifolium pratense

<400> SEQUENCE: 3
caacacagaa cttcaagcta gcataccaaa aaaaaaaaat ggtaaccatt atagcttctc      60
acactgtgat tccagaagaa ccaactccac aaggtccatt ttggctctct gatatggatc    120
aagtggttcg tatccgcgac gtaccaactc tttacattta caaaacacca agaaaaacc     180 aagaaaacaa aaacatagta gaaacctttaa aaaactctct aagcaaaatt cttgttcact    240
actatcctat agctggtaga ttgtgttaca tagaaggtgg tagattagaa ttgaatctca    300
atgcaaaagg agctattttg gttgaagctg aaacagaaaa aacaatgaat gattatggtg    360
acttttcaca ttttgacacc atcaaagaac ttgttccaat gattgattac aatcaaccaa    420
ttgaagaaat tccaaatttt gttgtgcaac tcaccaagtt caaaaacaat gaaggctttg    480
caattggtgt tgcttttctc catcctttat cagatggatt gggagccatt aaattcatca    540
actcatgggc caaatagca agaggtgaaa cacttgaggc taatgagtta ccattttgg     600 atagaaaact tctcaaattt tcacacacac ctttggagcc acgttttgaa cacttggagt    660
tgaagccact accactcatt ctaggtagaa agatgcaagt gaagaaaaa gagaagaaaa      720 cttcagcaac attgttgaaa ctttcatcag aacaagttga taagttaaag aaaaaagcca    780
atgaagaaga tgttctaggt gtccagaaaa agagtactc aaggccttat agtaaatttg     840
aagtaattag tgcacatata tggagatgtg catctaaggc acgtgagctt aaagataatc    900
aagaaagtgt tattagattt attgctgatg ttaaaaatag aatgattcca ccacttccta    960
aaaactattt tgggaatgct ttgactcaaa cagctactaa agggtatatt ggagaaatca   1020
catcaaagcc tttaggttac gtggcacaaa agataaggga agcaactgag ttggtaaatg   1080
atgagtatat aaggtcacaa attgatgttg ttagaagttt tgaacatttg gatgatgcac   1140
gaaaaatgtt tataggtgaa aaggctcgat attttggtaa tccaaatttt aatttgacta   1200
```

```
gttggttaag tatgcctgtt tatgaagctg attttggatg gggtaaacct aattactttg    1260
gattagctga tgtctcacca catgatagag ctgtcattct tcttagtcct gatgatgatg    1320
gatctgttct tgtgtctttc catcttcaga ttgcacatat ggagttttc aacaagtatt     1380 tttatgagga gatatgaaat aagggtggtt tttgggtcaa ttttttgaccc aaaatcaccc    1440 tctaagttgg t                                                          1451

<210> SEQ ID NO 4
<211> LENGTH: 452
<212> TYPE: PRT
<213> ORGANISM: Trifolium pratense

<400> SEQUENCE: 4

Met Val Thr Ile Ile Ala Ser His Thr Val Ile Pro Glu Glu Pro Thr
1               5                   10                  15

Pro Gln Gly Pro Phe Trp Leu Ser Asp Met Asp Gln Val Val Arg Ile
                20                  25                  30

Arg Asp Val Pro Thr Leu Tyr Ile Tyr Lys Thr Pro Lys Lys Asn Gln
            35                  40                  45

Glu Asn Lys Asn Ile Val Glu Thr Phe Lys Asn Ser Leu Ser Lys Ile
        50                  55                  60

Leu Val His Tyr Tyr Pro Ile Ala Gly Arg Leu Cys Tyr Ile Glu Gly
65                  70                  75                  80

Gly Arg Leu Glu Leu Asn Leu Asn Ala Lys Gly Ala Ile Leu Val Glu
                85                  90                  95

Ala Glu Thr Glu Lys Thr Met Asn Asp Tyr Gly Asp Phe Ser His Phe
            100                 105                 110

Asp Thr Ile Lys Glu Leu Val Pro Met Ile Asp Tyr Asn Gln Pro Ile
        115                 120                 125

Glu Glu Ile Pro Asn Phe Val Val Gln Leu Thr Lys Phe Lys Asn Asn
    130                 135                 140

Glu Gly Phe Ala Ile Gly Val Ala Phe Leu His Pro Leu Ser Asp Gly
145                 150                 155                 160

Leu Gly Ala Ile Lys Phe Ile Asn Ser Trp Ala Lys Ile Ala Arg Gly
                165                 170                 175

Glu Thr Leu Glu Ala Asn Glu Leu Pro Phe Leu Asp Arg Lys Leu Leu
            180                 185                 190

Lys Phe Ser His Thr Pro Leu Glu Pro Arg Phe Glu His Leu Glu Leu
        195                 200                 205

Lys Pro Leu Pro Leu Ile Leu Gly Arg Lys Asp Ala Ser Glu Glu Lys
    210                 215                 220

Glu Lys Lys Thr Ser Ala Thr Leu Leu Lys Leu Ser Ser Glu Gln Val
225                 230                 235                 240

Asp Lys Leu Lys Lys Lys Ala Asn Glu Glu Asp Val Leu Gly Val Gln
                245                 250                 255

Lys Lys Glu Tyr Ser Arg Pro Tyr Ser Lys Phe Glu Val Ile Ser Ala
            260                 265                 270

His Ile Trp Arg Cys Ala Ser Lys Ala Arg Glu Leu Lys Asp Asn Gln
        275                 280                 285

Glu Ser Val Ile Arg Phe Ile Ala Asp Val Lys Asn Arg Met Ile Pro
    290                 295                 300

Pro Leu Pro Lys Asn Tyr Phe Gly Asn Ala Leu Thr Gln Thr Ala Thr
305                 310                 315                 320
```

-continued

```
Lys Gly Tyr Ile Gly Glu Ile Thr Ser Lys Pro Leu Gly Tyr Val Ala
                325                 330                 335

Gln Lys Ile Arg Glu Ala Thr Glu Leu Val Asn Asp Glu Tyr Ile Arg
            340                 345                 350

Ser Gln Ile Asp Val Val Arg Ser Phe Glu His Leu Asp Asp Ala Arg
        355                 360                 365

Lys Met Phe Ile Gly Glu Lys Ala Arg Tyr Phe Gly Asn Pro Asn Phe
    370                 375                 380

Asn Leu Thr Ser Trp Leu Ser Met Pro Val Tyr Glu Ala Asp Phe Gly
385                 390                 395                 400

Trp Gly Lys Pro Asn Tyr Phe Gly Leu Ala Asp Val Ser Pro His Asp
                405                 410                 415

Arg Ala Val Ile Leu Leu Ser Pro Asp Asp Asp Gly Ser Val Leu Val
            420                 425                 430

Ser Phe His Leu Gln Ile Ala His Met Glu Leu Phe Asn Lys Tyr Phe
        435                 440                 445

Tyr Glu Glu Ile
    450

<210> SEQ ID NO 5
<211> LENGTH: 20
<212> TYPE: DNA
<213> ORGANISM: Artificial Sequence
<220> FEATURE:
<223> OTHER INFORMATION: synthesized

<400> SEQUENCE: 5
twytayccwd trgctgghmg                                                  20

<210> SEQ ID NO 6
<211> LENGTH: 23
<212> TYPE: DNA
<213> ORGANISM: Artificial Sequence
<220> FEATURE:
<223> OTHER INFORMATION: synthesized

<400> SEQUENCE: 6
aywgscytyc cmyawccaaa atc                                              23

<210> SEQ ID NO 7
<211> LENGTH: 19
<212> TYPE: DNA
<213> ORGANISM: Artificial Sequence
<220> FEATURE:
<223> OTHER INFORMATION: synthesized

<400> SEQUENCE: 7
amttcatcaa ywcatggkc                                                   19

<210> SEQ ID NO 8
<211> LENGTH: 23
<212> TYPE: DNA
<213> ORGANISM: Artificial Sequence
<220> FEATURE:
<223> OTHER INFORMATION: synthesized

<400> SEQUENCE: 8
ccaaaatcwg mwtcrtraah vgg                                              23

<210> SEQ ID NO 9
<211> LENGTH: 30
<212> TYPE: DNA
```

<213> ORGANISM: Trifolium pratense

<400> SEQUENCE: 9
ctggatacct agaacatctt cttcattggc               30

<210> SEQ ID NO 10
<211> LENGTH: 30
<212> TYPE: DNA
<213> ORGANISM: Trifolium pratense

<400> SEQUENCE: 10
cacctttgga gccacgtttt gaacacttgg               30

<210> SEQ ID NO 11
<211> LENGTH: 27
<212> TYPE: DNA
<213> ORGANISM: Artificial Sequence
<220> FEATURE:
<223> OTHER INFORMATION: synthesized

<400> SEQUENCE: 11
caacacagaa cttcaascta gcatacc                  27

<210> SEQ ID NO 12
<211> LENGTH: 26
<212> TYPE: DNA
<213> ORGANISM: Artificial Sequence
<220> FEATURE:
<223> OTHER INFORMATION: synthesized

<400> SEQUENCE: 12
accaacttag agggtgattt tgggtc                   26

<210> SEQ ID NO 13
<211> LENGTH: 30
<212> TYPE: DNA
<213> ORGANISM: Artificial Sequence
<220> FEATURE:
<223> OTHER INFORMATION: synthesized

<400> SEQUENCE: 13
cgggccatgg taaccattat agcttctcac               30

<210> SEQ ID NO 14
<211> LENGTH: 37
<212> TYPE: DNA
<213> ORGANISM: Artificial Sequence
<220> FEATURE:
<223> OTHER INFORMATION: synthesized

<400> SEQUENCE: 14
gggcctcgag tcatatctcc tcataaaaat acttgtt       37

<210> SEQ ID NO 15
<211> LENGTH: 36
<212> TYPE: DNA
<213> ORGANISM: Artificial Sequence
<220> FEATURE:
<223> OTHER INFORMATION: synthesized

<400> SEQUENCE: 15
gtctagaaaa caatggtaac cattatagct tctcac        36

<210> SEQ ID NO 16
<211> LENGTH: 34

```
<212> TYPE: DNA
<213> ORGANISM: Artificial Sequence
<220> FEATURE:
<223> OTHER INFORMATION: synthesized

<400> SEQUENCE: 16
cggtacctca tatctcctca taaaaatact tgtt                              34

<210> SEQ ID NO 17
<211> LENGTH: 25
<212> TYPE: DNA
<213> ORGANISM: Trifolium pratense

<400> SEQUENCE: 17
ggtgtgagtc acactgtgcc aatct                                        25

<210> SEQ ID NO 18
<211> LENGTH: 25
<212> TYPE: DNA
<213> ORGANISM: Trifolium pratense

<400> SEQUENCE: 18
cggaacctct cagctccaat tgtga                                        25
```